US011253519B2

(12) United States Patent
Miyata et al.

(10) Patent No.: US 11,253,519 B2
(45) Date of Patent: Feb. 22, 2022

(54) COMPOSITION USED TO IMPROVE SYMPTOMS OF AUTISM SPECTRUM DISORDER, AND METHOD USING SAME FOR IMPROVING SYMPTOMS OF AUTISM SPECTRUM DISORDER

(71) Applicant: RENASCIENCE CO., LTD., Tokyo (JP)

(72) Inventors: Toshio Miyata, Miyagi (JP); Shigeo Kure, Miyagi (JP); Shinichi Kuriyama, Miyagi (JP); Hiroki Sato, Miyagi (JP)

(73) Assignee: RENASCIENCE CO., LTD., Tokyo (JP)

( * ) Notice: Subject to any disclaimer, the term of this patent is extended or adjusted under 35 U.S.C. 154(b) by 572 days.

(21) Appl. No.: 16/081,705

(22) PCT Filed: Mar. 2, 2017

(86) PCT No.: PCT/JP2017/008355
§ 371 (c)(1),
(2) Date: Aug. 31, 2018

(87) PCT Pub. No.: WO2017/150686
PCT Pub. Date: Sep. 8, 2017

(65) Prior Publication Data
US 2020/0368233 A1 Nov. 26, 2020

(30) Foreign Application Priority Data
Mar. 2, 2016 (JP) .............................. JP2016-040492

(51) Int. Cl.
*A61K 31/51* (2006.01)
*A61P 25/00* (2006.01)
*A61K 31/44* (2006.01)
*A61K 9/00* (2006.01)

(52) U.S. Cl.
CPC ............ *A61K 31/51* (2013.01); *A61K 9/0053* (2013.01); *A61K 31/44* (2013.01); *A61P 25/00* (2018.01)

(58) Field of Classification Search
CPC ...... A61K 31/51; A61K 31/33; A61K 9/0053; A61P 25/00
USPC ........................................................ 514/276
See application file for complete search history.

(56) References Cited

U.S. PATENT DOCUMENTS

| 2002/0192310 A1 | 12/2002 | Bland et al. |
| 2005/0272781 A1 | 12/2005 | Khalifah et al. |
| 2008/0161398 A1 | 7/2008 | Verlaan et al. |
| 2011/0028470 A1 | 2/2011 | Itokawa et al. |
| 2011/0150968 A1 | 6/2011 | Grassi |
| 2011/0274679 A1 | 11/2011 | Pietrzkowski |
| 2013/0338574 A1 | 12/2013 | Kakuta et al. |
| 2014/0134222 A1 | 5/2014 | Morariu |
| 2014/0171472 A1 | 6/2014 | Degenhardt et al. |

FOREIGN PATENT DOCUMENTS

| CN | 103458891 | 12/2013 |
| CN | 107148272 | 9/2017 |
| EP | 3 187 185 | 7/2017 |
| JP | 11-512432 | 10/1999 |
| JP | 2002-527471 | 8/2002 |
| JP | 2009-39088 | 2/2009 |
| WO | 97/09981 | 3/1997 |
| WO | 00/23063 | 4/2000 |
| WO | 2008/049615 | 5/2008 |
| WO | 2012/011588 | 1/2012 |

OTHER PUBLICATIONS

Kamiyama et al., "A Clinical Study of Pyridoxine Treatment for Pervasive developmental disorders with Hypersensitivity to Sound", Official Journal of the Japanese Society of Child Neurology, vol. 38: 277-282 (2006).
Hunsinger et al., "Is there abasis for novel pharmacotherapy of autism?", Life Sciences, 67: 1667-1682 (2000).
Rossignol et al., "Novel and emerging treatments for autism spectrum disorders: A systemic review", Annals of Clinical Psychiatry, 21(4): 213-236 (2009).
Khahn et al., "The role of thiamine in autism", American Journal of Psychiatry and Neuroscience, 1(2): 22-37 (2013).
Diagnostic and Statistical Manual of Mental Disorders Fifth Edition, Feb. 15, 2015, vol. 1, pp. 31-32, 49-57.
"Pyridoxine treatment in a subgroup of children with pervasive developmental disorders", Developmental Medicine and Child Neurology, 44(4): 283-286 (2002).
Nye et al., "Combined vitamin B6-magnesium treatment in autism spectrum disorder (Review)", Cochrane Database of Systematic Reviews, issue 4, Art. CD003497. DOI10.1002/14651858.CD003497.pub2.
Grant-in-Aid for Scientific Research (KAKENHI) Research Result Report, May 2010.
Baxter et al., "Pyridoxine-dependent Seizures: Demographic, Clinical, MRI and Psychometric Features, and Effect of Dose on Intelligence Quotient", Developmental Medicine and Child Neurology, vol. 38: 998-1006 (1996)
Lofthouse et al., "A review of Complementary and Alternative Treatments for Autism Spectrum Disorders" Autism Research and Treatment, Article ID 870391, 1-21 (2012).
Rimland, "An Orthomolecular Study of Psychotic Children", Orthomolecular Psychiatry, 3(4): 371-377 (1974).

(Continued)

*Primary Examiner* — Yevgeny Valenrod
(74) *Attorney, Agent, or Firm* — Wenderoth, Lind & Ponack, L.L.P.

(57) ABSTRACT

The present invention provides a composition effective in improving symptoms of autism spectrum disorder. The composition contains at least one pyridoxamine compound selected from the group consisting of pyridoxamine and pharmaceutically acceptable salts thereof as an active substance. The composition may be used in combination with at least one thiamine compound selected from the group consisting of thiamine, derivatives thereof, and pharmaceutically acceptable salts thereof.

12 Claims, 17 Drawing Sheets

(56) References Cited

OTHER PUBLICATIONS

Merck Manual, 18th Edition, Japanese Version, 2007, pp. 39-40.
Japanese Office Action, dated Aug. 16, 2016, issued in corresponding Japanese Patent Application No. 2016-040492.
Shahmiri et al., "High-dose thiamine supplementation improves glucose tolerance in hyperglycemic individuals: a randomized, double-blind cross-over trial", European Journal of Nutrition, 52: 1821-1824 (2013).
Ahmed et al., "Advanced glycation endproducts: what is their relevance to diabetic complications?", Diabetes, Obesity and Metabolism, 9: 233-245 (2007).
U.S. Office Action, dated Jun. 6, 2018 for U.S. Appl. No. 15/507,057.
International Search Report, dated May 9, 2017 in corresponding International Patent Application No. PCT/JP2017/008355.
Extended European Search Report dated Mar. 14, 2018 in European Application No. 15835127.0.
Engelen et al., "Current therapeutic interventions in the glycation pathway: evidence from clinical studies", Diabetes, Obesity and Metabolism, 15(8): 677-689 (2013).
Nascimento et al., "Effect of High-Dose Thiamine and Pyridoxine on Advanced Glycation End Products and Other Oxidative Stress Markers in Hemodialysis Patients: A Randomized Placebo-Controlled Study", Journal of Renal Nutrition, 16(2): 119-124 (2006).
Booth et al., "Thiamine Pyrophosphate and Pyridoxamine Inhibit the Formation of Antigenic Advanced Glycation End-Products: Comparison with Aminoguanidine" Biochemical and Biophysical Research Communications, 220(1) 113-119 (1996).
Sell et al., "Structure Elucidation of a Senescence Cross-link from Human Extracellular Matrix", The Journal of Biological Chemistry, 264(36):21597-21602 (1989).
Takeuchi, "TAGE (toxic AGEs) hypothesis in life style-related disease", Bulletin of Hokuriku University, 28:33-48 (1994), with English Abstract & Partial English Translation.
Nagai et al., "Significance of Advanced Glycation End Products in Aging-Related Disease", Anti-Aging Medicine, 7(10):112-119 (2010).
Nakayama et al., "Plasma a-Oxoaldehyde Levels in Diabetic and Nondiabetic Chronic Kidney Disease Patients", American Journal of Nephrology, 28(6):871-878 (2008).
Ogawa et al., "Methylglyoxal Is a Predictor in Type 2 Diabetic Patients of Intima-Media Thickening and Elevation of Blood Pressure", Hypertension, 56(3):471-476 (2010).
Sundl et al., "Antioxidant Status of Patients on Peritoneal Dialysis: Associations with Inflammation and Glycoxidative Stress", Peritoneal Dialysis International, 29(1):89-101 (2009).
Kalovsova et al., "Advanced Glycation End-Products in Patients with Chronic Alcohol Misuse", Alcohol & Alcoholism, 39(4):316-320 (2004).
Junaid et al., "Proteomic Studies Identified a Single Nucleotide Polymorphism in Glyoxalase I as Autism Susceptibility Factor", American Journal of Medical Genetics Part A, 131(1):11-17 (2004).
International Search Report dated Dec. 1, 2015 in corresponding International (PCT) Application No. PCT/JP2015/073935.
Hamada, "Nerve tissue damage caused by thiamine (vitamin B1) deficiency ", *Comp. Physiol. Biochem.* 31(1):13-19, 2014, partial English translation.
Office Action dated Jan. 24, 2020 in European Patent Application No. 15 835 127.0.
Office Action dated Feb. 24, 2020 in corresponding U.S. Appl. No. 15/507,057.
Hagiwara et al., "Effects of pyridoxamine (K-163) on glucose intolerance and obesity in high-fat diet C57BL/6J mice", Metabolism Clinical and Experimental, 2009, vol. 58, pp. 934-945.
Office Action dated Apr. 14, 2020 in corresponding Chinese Patent Application No. 201580059256.2, with English translation.
Schopler, Eric et al., "Medical Treatment of Autistic People", in *Neurobiological Issues in Autism*, in, Plenum Press, New York, 1987, p. 381.
Arai, Makoto et al., "Schizophrenia and Carbonyl Stress", *Journal of Nerve*, 2012, vol. 114, pp. 101-106, with English Abstract.
Office Action dated Apr. 28, 2020 in corresponding Chinese Patent Application No. 201780015030.1, with English translation.
Supplementary European Search Report dated Oct. 1, 2019 in European Application No. 17760149.9.

Fig. 1

---
Autism Spectrum Disorder Diagnostic Criteria
299.00 (F84.0)

---

A. Persistent deficits in social communication and social interaction across multiple contexts, as manifested by the following, currently or by history (examples are illustrative, not exhaustive):

1. Deficits in social-emotional reciprocity, ranging, for example, from abnormal social approach and failure of normal back-and-forth conversation; to reduced sharing of interests, emotions, or affect; to failure to initiate or respond to social interactions.

2. Deficits in nonverbal communicative behaviors used for social interaction, ranging, for example, from poorly integrated verbal and nonverbal communication; to abnormalities in eye contact and body language, or deficits in understanding and use of gestures; to a total lack of facial expressions and nonverbal communication.

3. Deficits in developing, maintaining, and understanding relationships, ranging, for example, from difficulty adjusting behavior to suit various social contexts; to difficulty in sharing imaginative play or in making friends; to absence of interest in peers.

B. Restricted, repetitive patterns of behavior, interests, or activities, as manifested by at least two of the following, currently or by history (examples are illustrative, not exhaustive):

1. Stereotyped or repetitive motor movements, use of objects, or speech (e.g., simple motor stereotypes, lining up toys or flipping objects, echolalia, idiosyncratic phrases).

2. Insistence on sameness, inflexible adherence to routines, or ritualized patterns of verbal nonverbal behavior (e.g., extreme distress at small changes, difficulty with transitions, rigid thinking patterns, greeting rituals, need to take the same route or eat the same food every day).

3. Highly restricted, fixated interests that are abnormal in intensity or focus (e.g., strong attachment to or preoccupation with unusual objects, excessively circumscribed or perseverative interest).

4. Hyper- or hyporeactivity to sensory input or unusual interests in sensory aspects of the environment (e.g., apparent indifference to pain/temperature, adverse response to specific sounds or textures, excessive smelling or touching of objects, visual fascination with lights or movement).

(continued from Fig. 1)

C. Symptoms must be present in the early developmental period (but may not fully manifest until social demands exceed limited capacities, or may be masked by learned strategies in later life).

D. Symptoms cause clinically significant impairment in social, occupational, or other important areas of current functioning.

E. These disturbances are not better explained by intellectual disability (intellectual developmental disorder) or global developmental delay. Intellectual disability and autism spectrum disorder frequently co-occur; to make comorbid diagnoses of autism spectrum disorder and intellectual disability, social communication should be below that expected for general developmental level.

Note: Individuals with a well-established DSM-IV diagnosis of autistic disorder, Asperger's disorder, or pervasive developmental disorder not otherwise specified should be given the diagnosis of autism spectrum disorder. Individuals who have marked deficits in social communication, but whose symptoms do not otherwise meet the criteria for autism spectrum disorder, should be evaluated for social (pragmatic) communication disorder.

Fig. 2

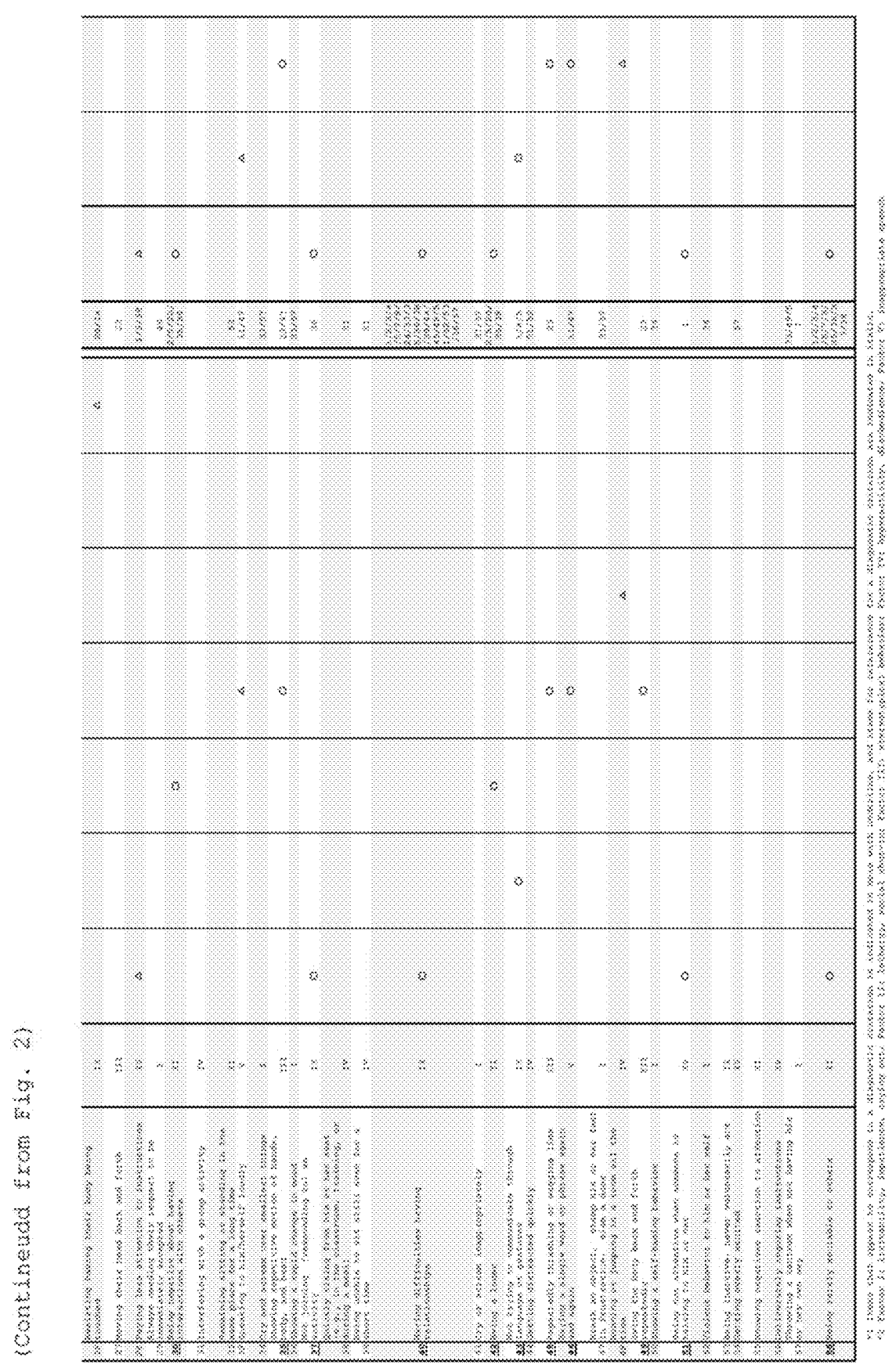

(Continued from Fig. 2)

Fig. 3

PARS-TR Item

| | | | |
|---|---|---|---|
| 1 | Making little or inconsistent eye contact | 30 | Being disgusted with a particular sound |
| 2 | Not showing interest in other children | 31 | Being insensitive or sensitive to pain or heat |
| 3 | Failing to respond to someone calling their name | 32 | Being terrified of nothing |
| 4 | Not bringing things that they want to show to others | 33 | Suddenly crying or becoming upset |
| 5 | Not sharing enjoyment of objects by pointing | 34 | Showing self-harming behaviors, such as hitting the head on the wall or biting a hand |
| 6 | Being slow in conversation | 35 | Having no friends of about the same age |
| 7 | Having difficulty with the back and forth of conversation | 36 | Showing self-centered behaviors, with no regard for surrounding people |
| 8 | Talking at length about a subject without noticing that others are uninterested, or without giving others a chance to respond | 37 | Showing interactive behaviors inappropriate for the context when approached by someone |
| 9 | Not playing a game of make-believe with friends | 38 | Interacting with others only when having a request |
| 10 | Often repeating someone's words in a parrot fashion | 39 | Having difficulty understanding what is said from one situation to another |
| 11 | Repeat a phrase from a commercial exactly as it is | 40 | Using big words, but not fully understanding the meaning thereof |
| 12 | Becoming caught up in sensory play | 41 | Difficulty understanding who is talking to who in a large group conversation |
| 13 | Having an intense interest in road signs, marks, numbers, and characters | 42 | Being incapable of explaining how and why |
| 14 | Showing an interest in watching a spinning object | 43 | Speaking in a unnatural and monotonous tone |
| 15 | Taking a side glance at an object, or looking at an object while holding it extremely close to the eyes | 44 | Having difficulty understanding another person's feeling or point of view |
| 16 | Getting caught up in an activity to line up toys or bottles | 45 | Having difficulty understanding jokes and irony, and interpreting them literally |
| 17 | Tiptoeing sometimes | 46 | Being keen on acquiring knowledge in a particular field, such as the names of places or train stations |
| 18 | Being hyperactive, and where he or she goes when their hand is let go of is unpredictable | 47 | Enacting a familiar scene from a TV show alone |
| 19 | Attempting to eat or swallow something inedible | 48 | Persistently and repeatedly harassing someone on purpose |
| 20 | Disliking being hugged | 49 | Always wanting to be the best |

(continued from Fig. 3)

| | | | |
|---|---|---|---|
| 21 | Watching a particular scene of a video repeatedly | 50 | Showing tic symptoms (e.g., blinking, head movements, abuseful language) |
| 22 | Fiddling with an object repeatedly in the same pattern, such as page-turning or tearing up paper | 51 | Being restless in a manner inappropriate for the context |
| 23 | Sometimes continuously moving the entire body or part of the body in the same pattern | 52 | Being very careless, unable to behave appropriately for the context |
| 24 | Disliking being touched | 53 | Showing behavioral arrest, and becoming incapable of moving to the next act or frozen |
| 25 | Persistently asking the same question | 54 | Appearing unashamed |
| 26 | Showing confusion when regular daily routines or procedures suddenly change | 55 | Being easily deceived |
| 27 | Having negative lifestyle habits, and being incapable of living independently | 56 | Being likely to feel victimized, suspicious, or aggressive |
| 28 | Becoming mentally unstable when recalling bad events in the past | 57 | Being emotionally unstable, and showing frequent emotional ups and downs |
| 29 | Showing extreme pickiness in food, with an extremely narrow range of food choice | | |

Fig. 4

| | | GRS-R | GGM-5 |
|---|---|---|---|
| II. Stereotypical Behavior | 1. Entire body (rocking, swinging) | | A1, B1 |
| | 2. Head (spinning, nodding, moving it from side to side) | | B1 |
| | 3. Hands and fingers (wave hands, wiggle fingertips or fiddle with fingertips, clap their hands, swing or wag their hands or arms) | | B1 |
| | 4. Full-body motion (run in a circular motion, twirl, jump, skip) | | B1, B2 |
| | 5. Use of an object (spin an object, fiddle with an object, bang an object, throw an object, drop an object held in their hand) | | B1, B2 |
| | 6. Sense (cover their eyes, look or stare at a hand or an object from a close distance, cover their ears, sniff an object, rub the surface of an object) | | B3, B4 |
| III. Self-Harming Behavior | 7. Pat themselves on part of their body (head, face, other part of the body) | | B1 |
| | 8. Hit their body on the surface of something or an object (hit their head or other part of their body on the surface of the table, floor, or other objects) | | B1 |
| | 9. Pat themselves with an object (hit their head or other part of their body with an object) | | B1 |
| | 10. Bite themselves (bite their hand, wrist, arm, lip, or tongue) | | B1 |
| | 11. Pull themselves (pull their hair or skin) | | B1 |
| | 12. Rub/scratch themselves (rub or scratch their arm, leg, face, or torso severely enough to get a bruise) | | B1 |
| | 13. Poke part of their body with a finger or an object (poke in the eye or ear) | | B1 |
| | 14. Pinch their skin (pinch the skin of their face, hand, arm, leg, or torso) | | B1 |

(continued from Fig. 4)

| Category | # | Description | Codes |
|---|---|---|---|
| III: Obsessive-Compulsive Behavior | 15 | Arrangement/order (place a particular object in a particular place or in a particular pattern; a desire for things to be equal or symmetrical) | B2 |
| | 16 | Perfection (a door must be opened or closed; place everything outside the container or outside their territory) | B2 |
| | 17 | Washing/cleaning (overly wash a part of their body; remove lint or a loose thread) | B2 |
| | 18 | Check (repeatedly check the door, window, drawer, electronic appliances, watch, key, or other things) | B2 |
| | 19 | Counting (count items; count until a certain number, count in a particular way) | B2 |
| | 20 | Hoarding (collect, hoard, or hide particular items) | B2 |
| | 21 | Repetition (a desire for repeating a certain pattern of motion; come in and out through a door, alternate between standing and sitting, put on and take off their clothes) | B1, B2 |
| | 22 | Touching/patting (a desire to pat or rub an object, surface, or a person) | B4 |
| IV: Ritualized Behavior | 23 | Eating (a strong preference or desire for eating or drinking a particular item; having a specific order in which he or she eats or drinks a food or drink; a strong desire for arranging items related to eating in a particular pattern) | B2, B3, B4 |
| | 24 | Sleep/bedtime (a strong desire for a particular routine before bedtime, a strong desire to arrange items in the room in "exactly the right way" before going to bed, a strong desire for a particular item to be placed beside him/her during sleep; a strong desire for someone to be beside him/her before or during sleep) | B2, B3 |
| | 25 | Self-care, bathing and changing clothes (a strong desire for a particular order in use of a bath, i.e., washing the body, taking a shower, taking a bath, and changing clothes; a strong desire for the same arrangement of bath items, or a strong desire to not move a particular item in the bathroom; a strong desire to wear particular clothes) | B2, B3 |
| | 26 | Outing/transfer (a strong desire to take a particular route or street; a strong desire to sit in a particular seat in a vehicle, or take a particular item (e.g., toys, cloth) with him/her when travelling; a strong desire for looking at or touching a sign, a particular item in a shop, or a particular place when travelling) | B2, B3, B4 |
| | 27 | Play/spare time (a strong desire for a particular form of play, a strong desire to follow a routine during play or in spare time; a strong desire to keep a particular item in sight/within reach during play or in spare time, strongly requires others do a particular thing during play) | B2, B3 |
| | 28 | Communication/interaction (repetitive behavior of asking a question, such as repeatedly talking about the same subject during conversation, a strong desire to talk about a particular subject; a strong desire to make someone talk about a particular thing during conversation, or make someone answer in a particular way) | A1, A2, A3, B2 |
| V: Insistence on Sameness | 29 | A strong desire to always have an object positioned in the same place (e.g., toys, daily essentials, furniture, paintings, etc.) | B2 |
| | 30 | Showing resistance to visiting a new place | B2 |
| | 31 | Getting upset when what he or she is doing is interrupted | B2 |
| | 32 | A strong desire to walk in a particular pattern (e.g., walking linearly) | B2 |
| | 33 | A strong desire to sit in the same seat | B2 |
| | 34 | Disliking changes in appearance or behavior in surrounding people | B2 |
| | 35 | A strong desire to use a particular door | B2 |
| | 36 | Liking to continue listening to the same CD, tape, record, or music; or watching the same movie or video, or a particular scene of a movie or video | B2, B3, B4 |
| | 37 | Resistance in changing activities; difficulty in transferring from one activity to another | B2, B3 |
| | 38 | A strong desire to do the same routine, household chores, daily duties in school or job every day | B2 |
| | 39 | A strong desire for a particular event to happen at a particular time | B2 |
| VI: Circumscribed Interests | 40 | Being enthusiastic about or caught up in one subject or activity (e.g., trains, computers, weather, or dinosaurs) | B3 |
| | 41 | Showing a strong attachment to a particular thing | B3 |
| | 42 | Being enthusiastic about a detail rather than the entirety of an object (e.g., buttons of clothing, or tires of a toy car) | B3, B4 |
| | 43 | Being enthusiastic about or caught up in a moving object (e.g., a ventilation fan or a clock) | B3, B4 |

Fig. 7
A
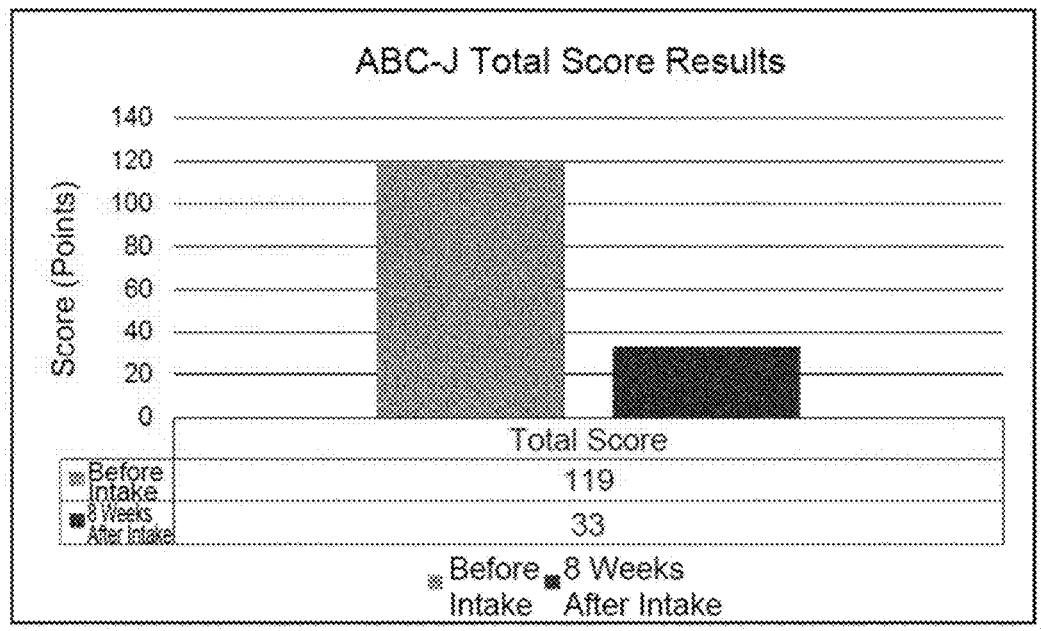
B
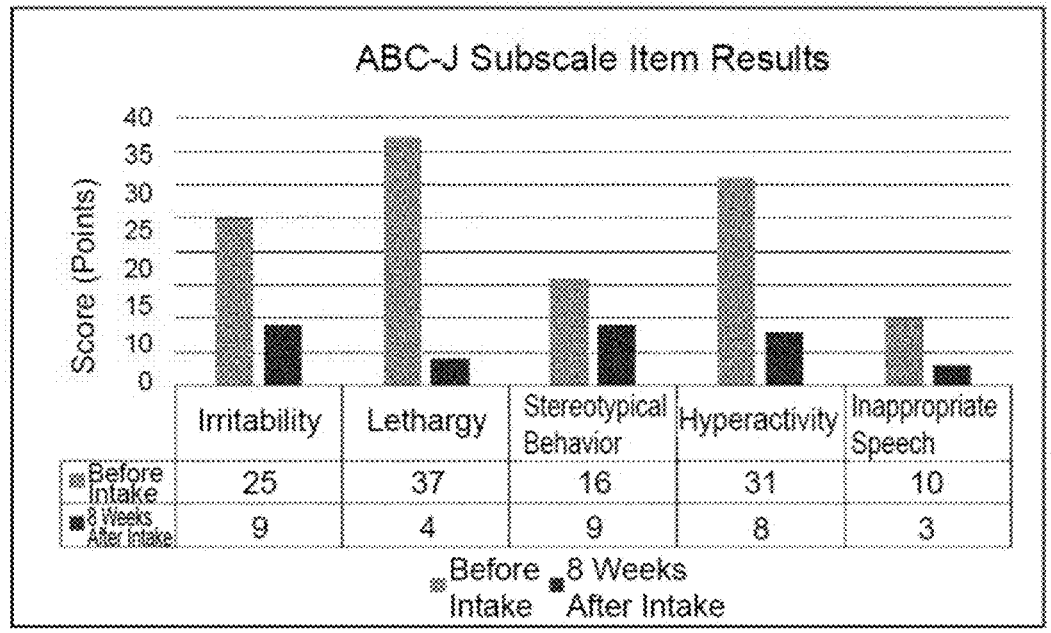

Fig. 8
A
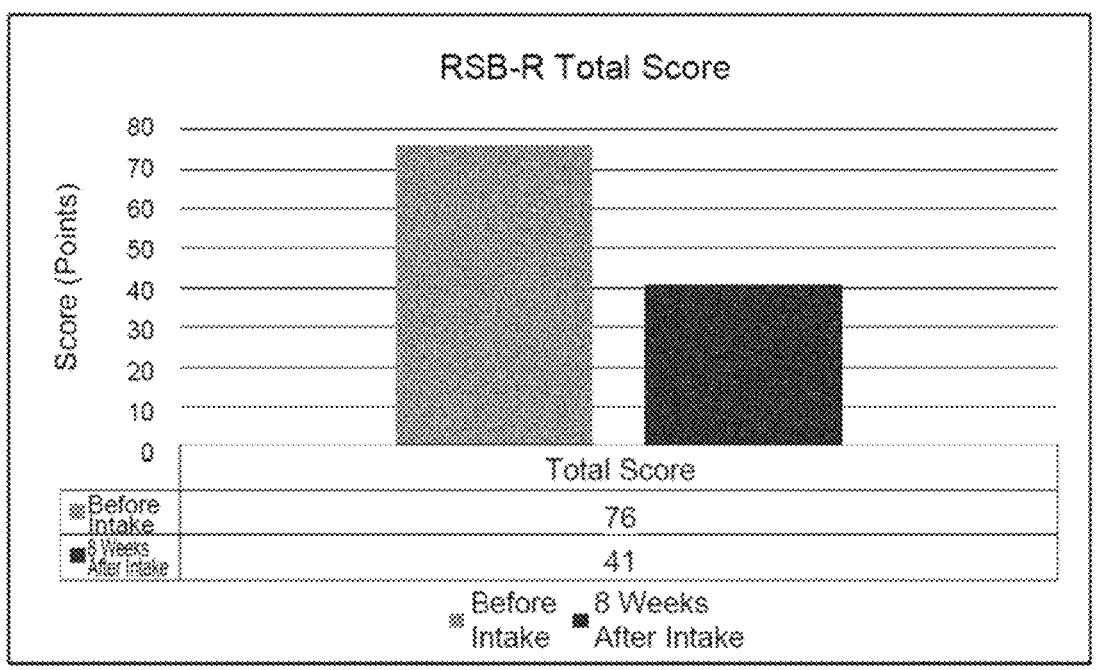
B
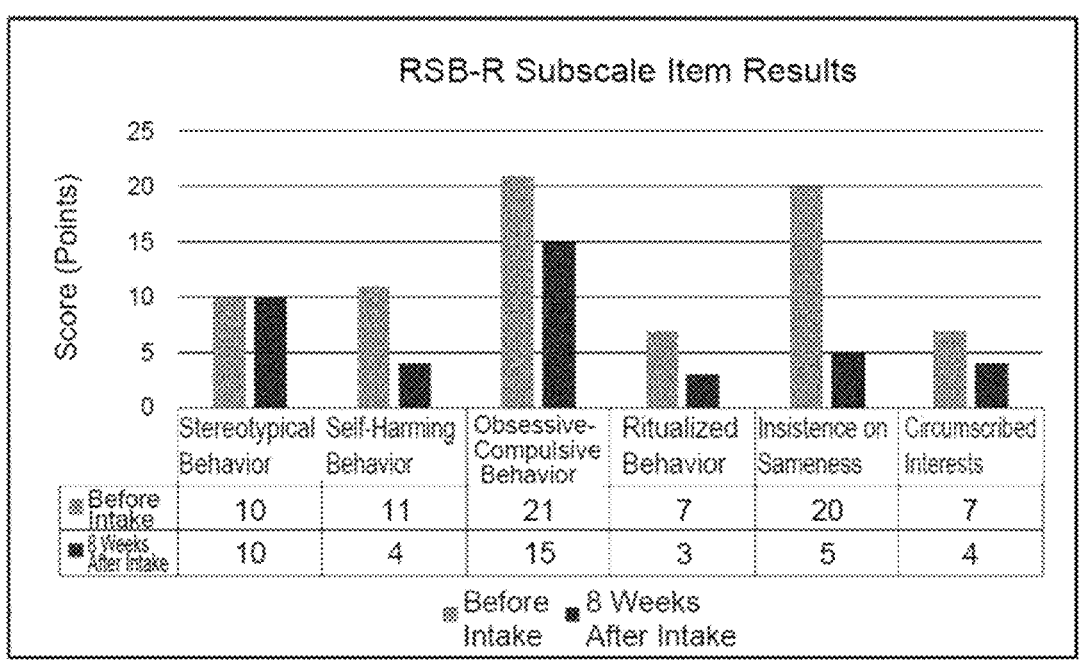

Fig. 9
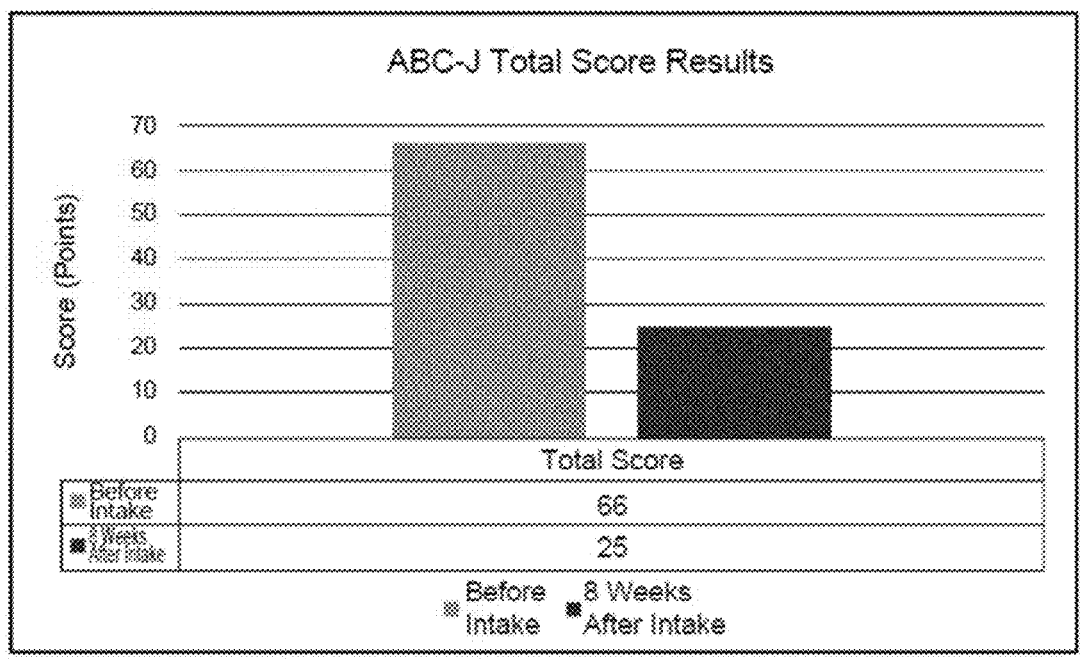
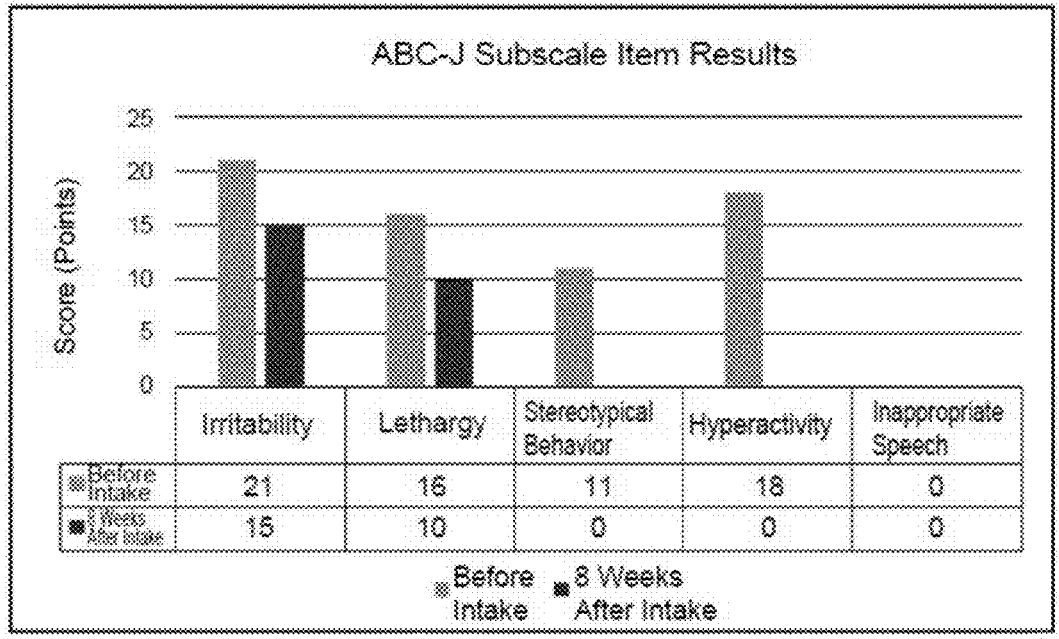

Fig. 10
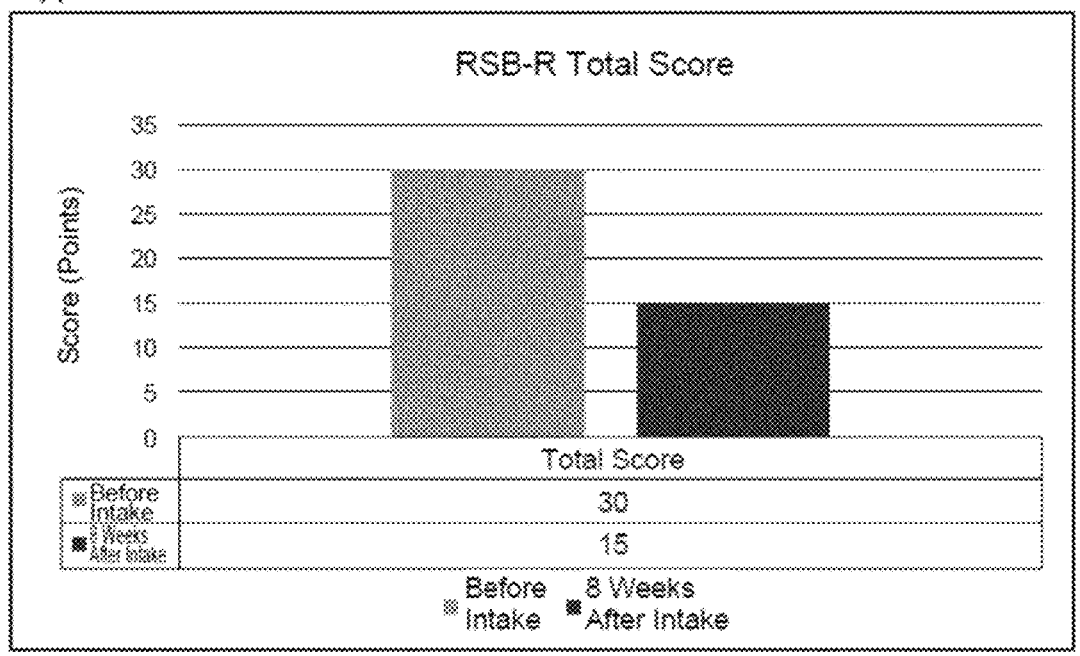
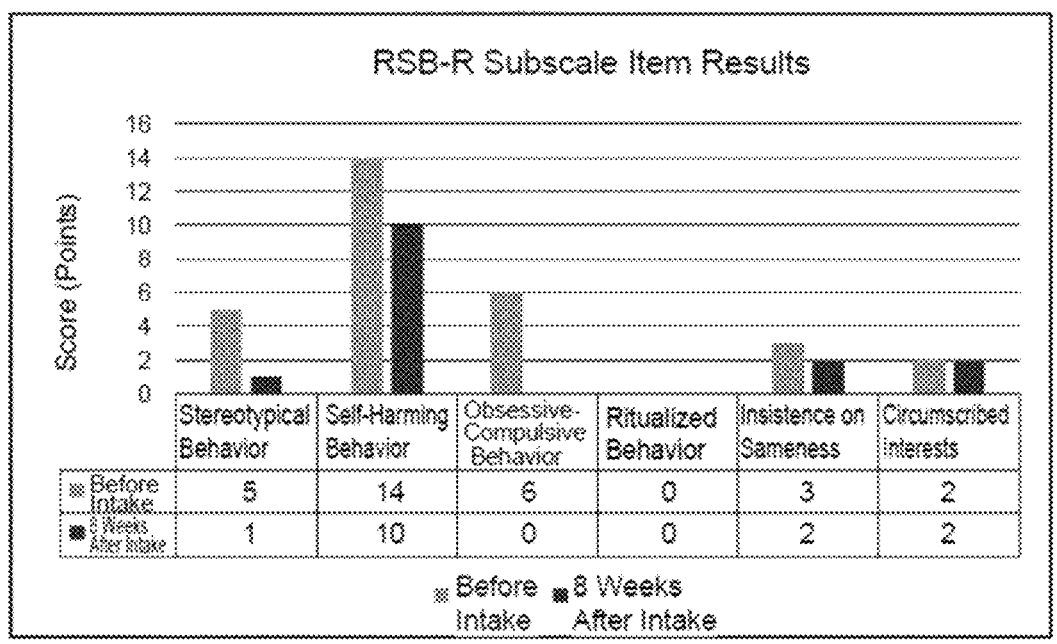

Fig. 12

Fig. 13
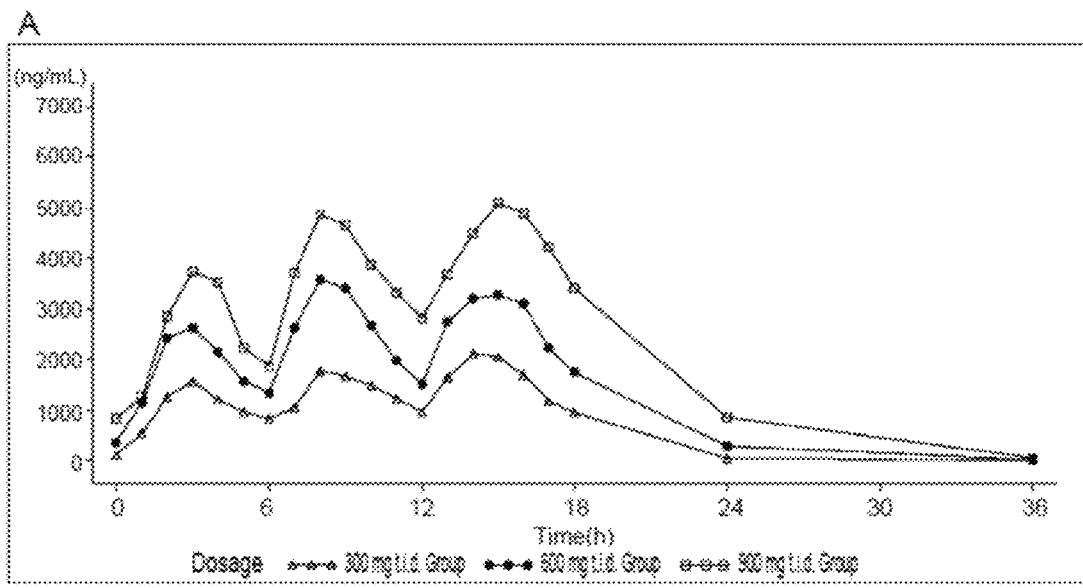
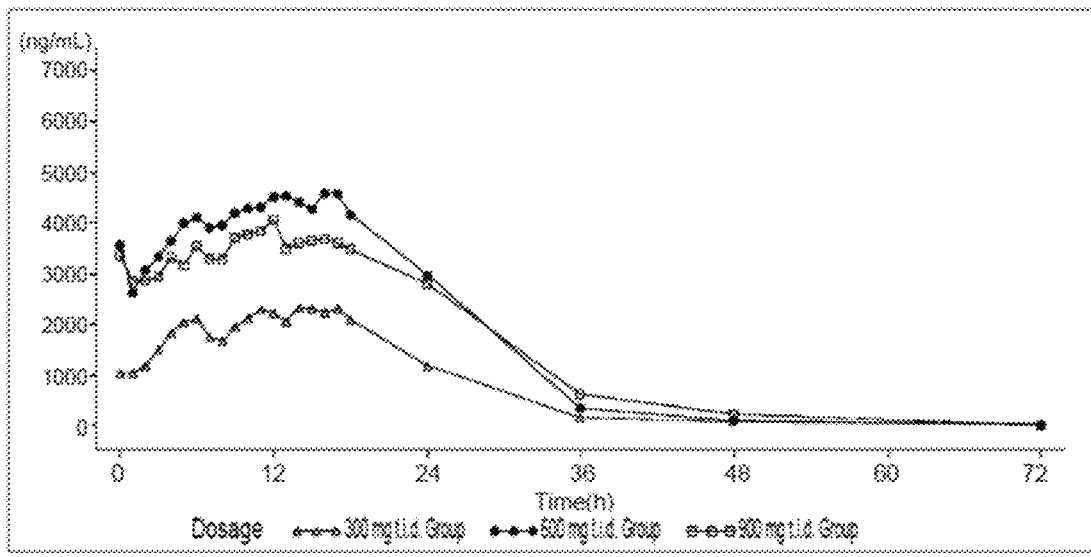

Fig. 14
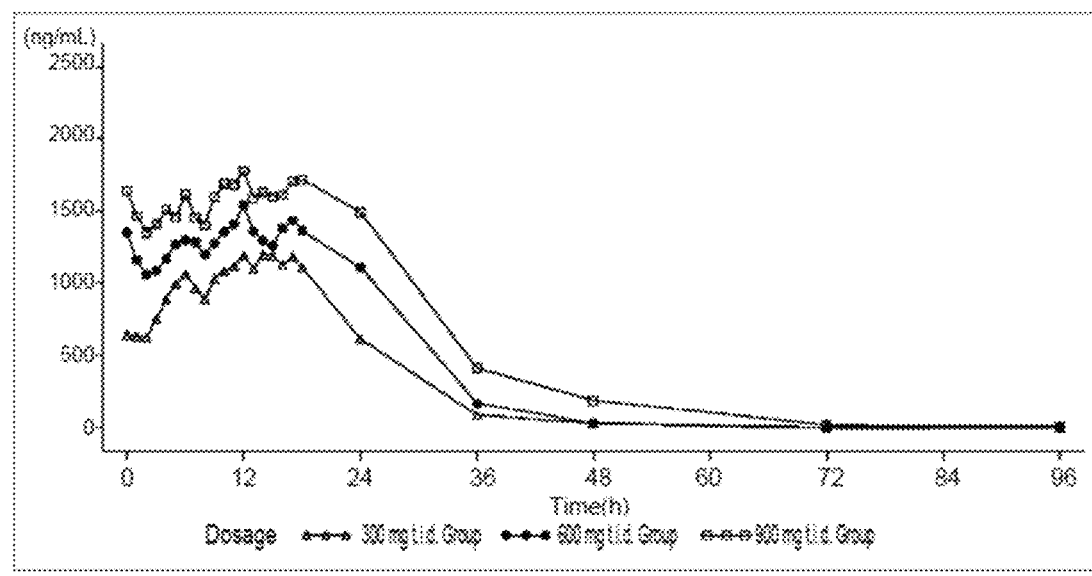
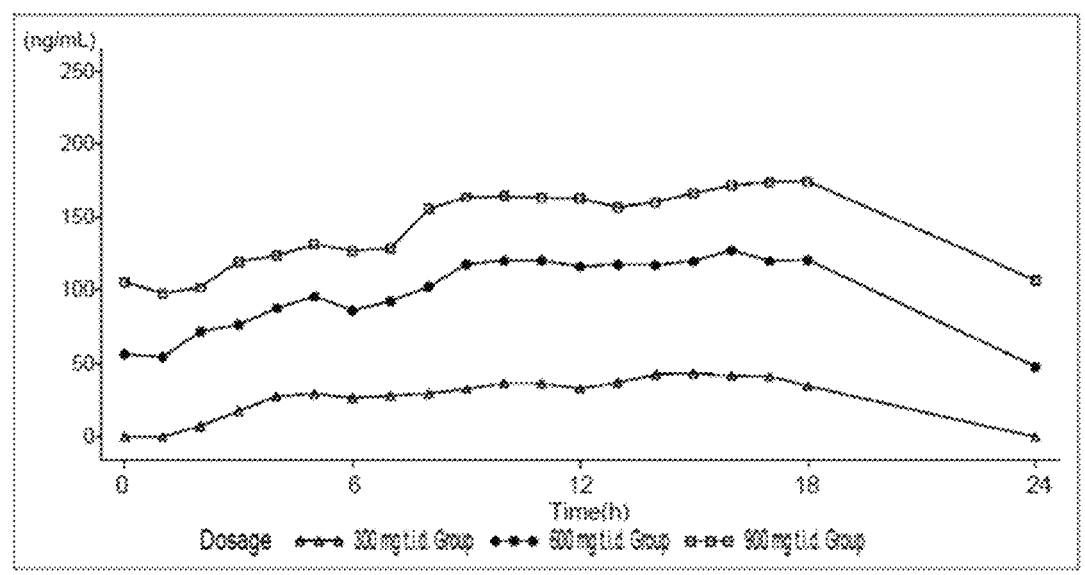

COMPOSITION USED TO IMPROVE SYMPTOMS OF AUTISM SPECTRUM DISORDER, AND METHOD USING SAME FOR IMPROVING SYMPTOMS OF AUTISM SPECTRUM DISORDER

TECHNICAL FIELD

The present invention relates to a composition for use in inhibiting or improving the symptoms of autism spectrum disorder. The invention also relates to a method for inhibiting or improving the symptoms of autism spectrum disorder. Autism spectrum disorder is also called "autism spectrum disease"; however, this invention and specification refer to it as autism spectrum disorder, or its abbreviation "ASD."

BACKGROUND ART

According to the Diagnostic and Statistical Manual of Mental Disorders (DSM, fifth edition (DSM-5), issued in 2013) disclosed in NPL 1 and other literature, ASD includes deficits in developing, maintaining, and understanding non-verbal communicative behaviors used in human-to-human reciprocity and interaction, as well as in personal relationships, and is characterized by persistent deficits in social communication and human-to-human interaction in multiple social contexts. Thus, a diagnosis of ASD is made largely based on the foundational characteristics "deficits in social communication and social interaction" (diagnostic criteria A) and "restricted, repetitive patterns or stereotyped patterns of behavior, interests, or activities" (diagnostic criteria B). These symptoms manifest in the early childhood, and restrict or impair everyday activities (diagnostic criteria C and D). The functional deficits may develop in different aspects, depending on individual traits and environment. Although the major diagnostic characteristics typically manifest in the developmental period, they may be hidden by therapeutic intervention, compensation, or support received. The signs of the disorder also greatly vary depending on the severity of the autistic symptoms, developmental stage, and chronological age. Accordingly, the condition is expressed by the term "spectrum." ASD comprehensively covers disorders that were previously referred to as early infantile autism, Kanner-type autism, high-functioning autism, atypical autism, pervasive developmental disorder not otherwise specified, childhood disintegrative disorder, and Asperger disorder (according to NPL 1).

A range of proposals have been made for the purpose of improving the symptoms of ASD. For example, regarding the technique related to the present invention, NPL 2 discloses that among children diagnosed with pervasive developmental disorder, such as ASD and Asperger syndrome, those, in particular, who are sensitive to sound and have expressive language disorder and dyspraxia, were administered a high amount of pyridoxine (vitamin $B_6$); and that increases in intelligence quotient (IQ) scores, which indicate improvement in the disorder, were observed. NPL 3 also discloses that a high dose of pyridoxine (vitamin B) was administered to children diagnosed with ASD to improve their communication and language. However, NPL 3 discloses that a high dose of pyridoxine also causes undesired side effects to develop, and that adult ASD patients as well as children with ASD were administered pyridoxine and Mg in combination to improve symptoms of ASD, while alleviating these side effects. Additionally, NPL 4 discloses, citing NPL 2 and NPL 5, that high doses of pyridoxine (vitamin $B_6$) are effective not only in improving vitamin $B_6$-dependent seizures that are similar to ASD in mental and physical characteristics, but also in improving symptoms of children with ASD having sensitivity to sound, expressive language disorder, and dyspraxia.

In addition to the above-described report of efficacy of high doses of pyridoxine in treating specific symptoms of ASD patients, there is also a study reporting that pyridoxal in a dosage of 30 mg/kg/day was effective in treating repetitive patterns of behavior of ASD patients. However, there is also research that denies this efficacy, and these medicinal substances (pyridoxine and pyridoxal) are not in common use as typical therapeutic medicines for ASD (NPL 6).

NPL 7 discloses that when administered pyridoxine, children with pervasive developmental disorder who have sensitivity to sound showed improvement in verbal intelligence. However, NPL 8, and NPL 9, which is cited by NPL 8, disclose that administering pyridoxine to children with ASD may cause side effects to develop (the development of symptoms such as irritability, hyperactivity, sound sensitivity, and enuresis, which coincide with or are similar to symptoms or problematic behaviors of ASD). NP 10 also suggests the potential of developing neurological disorder by administration of high doses of pyridoxine. However, NPL 8 reports, as does NPL 3, that the use of Mg in combination with pyridoxine can reduce these side effects caused by administration of pyridoxine; and improve speech, behaviors in social relationships, and other autistic behaviors of children with ASD. However, NPL 10 states, regarding the therapy with both pyridoxine and Mg, that the effect is not reproducible and thus questionable, and that some of these study reports include methodological flaws.

As noted above, NPL 8 to 10 suggest that administration of pyridoxine is not necessarily effective in improving ASD (even when administered in combination with Mg). Additionally, these studies also suggest the potential risk of deteriorating symptoms or problematic behaviors of ASD by administration of pyridoxine alone, in particular administration of pyridoxine to children or administration of high doses of pyridoxine. When all of these reports are considered, the administration of pyridoxine does not appear to be effective in improving symptoms of ASD, which is why pyridoxine is not prevalent as a drug for improving symptoms of ASD.

Pyridoxamine, which is a compound typically lumped into the group of vitamin $B_6$ or vitamin $B_6$ isoforms including pyridoxine and pyridoxal described above, is clearly distinguished, because of its amino group, from pyridoxine and pyridoxal, which have no amino group. Additionally, pyridoxamine, due to its lack of a carbonyl group, is clearly distinguished from pyridoxal and its metabolite (pyridoxal phosphate), which have a carbonyl group. Pyridoxamine is a substance with inherent properties that differ from those of pyridoxine or pyridoxal, in that it inhibits harmful protein (enzyme) modification by a carbonyl compound; and further repairs the protein modification (decarbonylation reaction), playing a role as an agent for eliminating carbonyl stress in vivo (NPL 6). Pyridoxamine has not yet been approved as a medicinal agent in Japan, or even in other countries.

NPL 2 to 10 merely mention the effect of pyridoxine in improving symptoms of ASD, and nowhere disclose or suggest pyridoxamine.

CITATION LIST

Non-Patent Literature

NPL 1: DSM-5®, Diagnostic and Statistical Manual of Mental Disorders, pp. 31-32, pp. 49-57, Japanese-language version, The Japanese Society of Psychiatry and Neurology, issued by Igaku-Shoin Ltd., Feb. 15, 2015, first edition, fourth impression NPL 2: Shinichi Kuriyama et al., Pyridoxine treatment in a subgroup of children with pervasive developmental disorders, Developmental Medicine & Child Neurology (2002), 44: 283-286

NPL 3: Nye C, Brice A, Combined vitamin $B_6$-magnesium treatment in autism spectrum disorder (Review), Cochrane Database of Systematic Reviews 2005, Issue 4, Art. CD003497. DOI:10.1002/14651858.CD003497 pub2.

NPL 4: Prepared on May 27, 2010, a report of research findings supported by a science research grant, research period: the years 2007 to 2009, research subject: Effects of vitamin $B_6$ on children with autism: a randomized controlled trial; research supervisor: Shinichi Kuriyama (Tohoku University School of Medicine)

NPL 5: Developmental Medicine & Child Neurology (1996), 38: 998-1006

NPL 6: N Lofthouse, R Hendren, E Hurt, L E Arnold, E Butter. A Review of Complementary and Alternative Treatments for Autism Spectrum Disorders, Autism Res Treat 2012; 28: 384-390

NPL 7: Machiko Kamiyama et al., A clinical Study of Pyridoxine Treatment for Pervasive Developmental Disorders with Hypersensitivity to Sound, No To Hattatsu [Brain and Development] 2006, Vol. 38, pp. 277-282

NPL 8: Daniel A, Rossignol, M D, FAAFP, Novel and emerging treatments for autism spectrum disorders: A systematic review, Anneals of Clinical Psychiatry, Vol. 21, No. 4, 2009

NPL 9: Bernard Rimland, An Orthomolecular Study of Psychotic Children, Orthomolecular Psychiatry 1974, 3, 371-377 NPL 10: Dina M. Hunsinger et al., Is there a basis for novel pharmacotherapy of autism?, Life Sciences, 67 (2000), 1667-1682

SUMMARY OF INVENTION

Technical Problem

An object of the present invention is to provide a composition suitably usable in inhibiting or improving symptoms of ASD. Another object of the invention is to provide a composition capable of inhibiting or improving symptoms of ASD, while preventing the development of vitamin $B_1$ deficiency caused by the administration of a certain amount or more of a pyridoxamine compound. Another object of the invention is to provide a method for inhibiting or improving symptoms of ASD of ASD patients. In particular, another object of the invention is to provide a method for inhibiting or improving symptoms of ASD, while preventing the development of vitamin $B_1$ deficiency caused by the administration of a certain amount or more of a pyridoxamine compound.

Solution to Problem

The present inventors conducted extensive research, and found that a pyridoxamine compound is highly effective in improving the symptoms of ASD. However, the administration of a pyridoxamine compound in a certain amount or more involves a potential risk of developing vitamin $B_1$ deficiency, such as Wernicke's encephalopathy, and symptoms of ASD must be inhibited or improved while this deficiency is also prevented. The present invention was completed on the basis of these findings and this demand, and includes the following aspects.

(I) Composition for Inhibiting or Improving Symptoms of ASD (I-1) A composition for inhibiting or improving symptoms of ASD, the composition comprising as an active substance at least one pyridoxamine compound selected from the group consisting of pyridoxamine and pharmaceutically acceptable salts thereof.

(I-2) The composition for inhibiting or improving symptoms of ASD according to (I-1), wherein the symptom of ASD is a deficit in social communication and social interaction, which is diagnostic criteria A of DSM-5, and/or a restricted, repetitive pattern or stereotyped pattern of behavior, interests, or activities, which is diagnostic criteria B of DSM-5.

(I-3) The composition according to (I-1) or (I-2), wherein the daily dose (or intake) of the at least one pyridoxamine compound is, on a pyridoxamine amount basis, 10 mg or more when the composition is a food or drink composition, and 300 mg or more when the composition is an oral pharmaceutical composition.

(I-4) The composition according to any one of (I-1) to (I-3), which is administered to a subject diagnosed with ASD in combination with at least one thiamine compound selected from the group consisting of thiamine, derivatives thereof, and pharmaceutically acceptable salts thereof.

(I-5) The composition according to any one of (I-1) to (I-4), which is a combination of (1) at least one pyridoxamine compound selected from the group consisting of pyridoxamine and pharmaceutically acceptable salts thereof, and (2) at least one thiamine compound selected from the group consisting of thiamine, derivatives thereof, and pharmaceutically acceptable salts thereof.

(I-6) The composition according to (I-5), wherein the daily dose (or intake) of the at least one thiamine compound is 1 to 500 mg on a thiamine amount basis.

(I-7) The composition according to any one of (I-1) to (I-6), which is an orally administered drug or a food or drink.

(I-8) The composition according to any one of (I-5) to (I-7), wherein the daily dose of (2) the at least one thiamine compound is 1 to 20 parts by weight, per 100 parts by weight of the daily dose of (1) the at least one pyridoxamine compound.

(I-9) The composition according to any one of (I-5) to (I-8), wherein (1) the at least one pyridoxamine compound and (2) the at least one thiamine compound are each packaged alone or with a pharmaceutically acceptable carrier or additive in separate preparations; and the at least one pyridoxamine compound or the preparation containing the at least one pyridoxamine compound and the at least one thiamine compound or the preparation containing the at least one thiamine compound are administered to a subject at different times, simultaneously, or in parallel.

(I-10) The composition according to (I-9), wherein the at least one pyridoxamine compound or the preparation containing the at least one pyridoxamine compound is administered to a subject before administration of the at least one thiamine compound or the preparation containing the at least one thiamine compound, or the at least one pyridoxamine compound or the preparation containing the at least one pyridoxamine compound is administered to a subject after administration of the at least one thiamine compound or the preparation containing the at least one thiamine compound.

(I-11) The composition according to any one of (I-5) to (I-9), which is a combination drug prepared as a single preparation comprising (1) the at least one pyridoxamine compound and (2) the at least one thiamine compound.

(II) Composition for Use in Inhibition or Improvement of Symptoms of ASD (Composition for Inhibiting or Improving Symptoms of ASD)

(II-1) A composition for use in the inhibition or improvement of symptoms of ASD, comprising at least one pyridoxamine compound selected from the group consisting of pyridoxamine and pharmaceutically acceptable salts thereof as an active substance.

(II-2) The composition for use in the inhibition or improvement of symptoms of ASD according to (II-1), which is administered to a subject having symptoms of ASD, preferably a subject diagnosed with ASD, in combination with at least one thiamine compound selected from the group consisting of thiamine, derivatives thereof, and pharmaceutically acceptable salts thereof, wherein the term "a subject" as used herein includes a human and a non-human mammal, and the phrase "a subject diagnosed with ASD" includes an ASD patient; the same applies hereinafter.

(II-3) The composition for use in the inhibition or improvement of symptoms of ASD according to (II-1) or (II-2), which is a combination of (1) the at least one pyridoxamine compound selected from the group consisting of pyridoxamine and pharmaceutically acceptable salts thereof, and (2) the at least one thiamine compound selected from the group consisting of thiamine, derivatives thereof, and pharmaceutically acceptable salts thereof.

(II-4) The composition for use in the inhibition or improvement of symptoms of ASD according to any one of (II-1) to (II-3), wherein the symptom of ASD is a deficit in social communication and social interaction, which is diagnostic criteria A of DSM-5 and/or a restricted, repetitive pattern or stereotyped pattern of behavior, interests, or activities.

(II-5) The composition for use in the inhibition or improvement of symptoms of ASD according to any one of (II-1) to (II-4), wherein the daily dose (or intake) of the at least one pyridoxamine compound is, on a pyridoxamine amount basis, 10 mg or more when the composition is a food or drink, and 300 mg or more when the composition is an orally administered drug.

(II-6) The composition for use in the inhibition or improvement of symptoms of ASD according to any one of (II-2) to (II-5), wherein the daily dose (or intake) of the at least one thiamine compound is 1 to 500 mg on a thiamine amount basis.

(II-7) The composition for use in the inhibition or improvement of symptoms of ASD according to any one of (II-3) to (II-6), wherein the daily dose of (2) the at least one thiamine compound is 1 to 20 parts by weight, per 100 parts by weight of the daily dose of (1) the at least one pyridoxamine compound.

(II-8) The composition for use in the inhibition or improvement of symptoms of ASD according to any one of (II-3) to (II-7), wherein (1) the at least one pyridoxamine compound and (2) the at least one thiamine compound are each packaged alone, or with a pharmaceutically acceptable carrier or additive in separate preparations; and the at least one pyridoxamine compound or the preparation containing the at least one pyridoxamine compound and the at least one thiamine compound or the preparation containing the at least one thiamine compound are administered to a subject at different times, simultaneously, or in parallel.

(II-9) The composition for use in the inhibition or improvement of symptoms of ASD according to (II-8), wherein the at least one pyridoxamine compound or the preparation containing the at least one pyridoxamine compound is administered to a subject before administration of the at least one thiamine compound or the preparation containing the at least one thiamine compound, or the at least one pyridoxamine compound or the preparation containing the at least one pyridoxamine compound is administered to a subject after administration of the at least one thiamine compound or the preparation containing the at least one thiamine compound.

(II-10) The composition for use in the inhibition or improvement of symptoms of ASD according to any one of (II-3) to (II-8), which is a combination drug prepared as a single preparation comprising (1) the at least one pyridoxamine compound and (2) the at least one thiamine compound.

(II-11) The composition for use in the inhibition or improvement of symptoms of ASD according to any one of (11-1) to (11-10), which is an orally administered drug or a food or drink.

(III) Use of Pyridoxamine Compound or Composition Comprising Pyridoxamine Compound in Production of Composition for Inhibiting or Improving Symptoms of ASD (III-1) Use of at least one pyridoxamine compound selected from the group consisting of pyridoxamine and pharmaceutically acceptable salts thereof or a composition comprising the at least one pyridoxamine compound in the production of a composition for the inhibition or improvement of symptoms of ASD, wherein the phrase "a composition for the inhibition or improvement of symptoms of ASD" as used herein refers to a composition for use in the inhibition or improvement of symptoms of ASD.

(III-2) The use according to (III-1), wherein the composition for the inhibition or improvement of symptoms of ASD is administered to a subject having symptoms of ASD, preferably a subject diagnosed with ASD; the composition is a combination of (1) the at least one pyridoxamine compound selected from the group consisting of pyridoxamine and pharmaceutically acceptable salts thereof or a composition containing the at least one pyridoxamine compound, and (2) the at least one thiamine compound selected from the group consisting of thiamine, derivatives thereof, and pharmaceutically acceptable salts thereof; and the term "a subject" includes a human and a non-human mammal, and the phrase "a subject diagnosed with ASD" includes an ASD patient.

(III-3) Use of a combination of the following (1) and (2) in the production of a composition for the inhibition or improvement of symptoms of ASD:

(1) at least one pyridoxamine compound selected from the group consisting of pyridoxamine and pharmaceutically acceptable salts thereof, and (2) at least one thiamine compound selected from the group consisting of thiamine, derivatives thereof, and pharmaceutically acceptable salts thereof.

(III-4) The use according to any one of (III-1) to (III-3), wherein the symptom of ASD is a deficit in social communication and social interaction and/or a restricted, repetitive pattern or stereotyped pattern of behavior, interests, or activities.

(III-5) The use according to any one of (III-1) to (III-4), wherein the daily dose (or intake) of the at least one pyridoxamine compound in the composition for the inhibition or improvement of symptoms of ASD is, on a pyridoxamine amount basis, 10 mg or more when the composition is a food or drink, and 300 mg or more when the composition is an orally administered drug.

(III-6) The use according to any one of (III-2) to (III-5), wherein the daily dose (or intake) of the at least one thiamine compound in the composition for the inhibition or improvement of symptoms of ASD is 1 to 500 mg on a thiamine amount basis.

(III-7) The use according to any one of (III-2) to (III-6), wherein the daily dose of (2) the at least one thiamine compound is 1 to 20 parts by weight, per 100 parts by weight of the daily dose of (1) the at least one pyridoxamine compound.

(III-8) The use according to any one of (III-2) to (III-7), wherein (1) the at least one pyridoxamine compound and (2) the at least one thiamine compound are each packaged alone, or with a pharmaceutically acceptable carrier or additive in separate preparations; and the at least one pyridoxamine compound or the preparation containing the at least one pyridoxamine compound and the at least one thiamine compound or the preparation containing the at least one thiamine compound are administered to a subject at different times, simultaneously, or in parallel.

(III-9) The use according to (III-8), wherein the at least one pyridoxamine compound or the preparation containing the at least one pyridoxamine compound is administered to a subject before administration of the at least one thiamine compound or the preparation containing the at least one thiamine compound, or the at least one pyridoxamine compound or the preparation containing the at least one pyridoxamine compound is administered to a subject after administration of the at least one thiamine compound or the preparation containing the at least one thiamine compound.

(III-10) The use according to any one of (III-2) to (III-7), wherein the composition for the inhibition or improvement of symptoms of ASD is a combination drug prepared as a single preparation comprising (1) the at least one pyridoxamine compound and (2) the at least one thiamine compound.

(III-11) The use according to any one of (III-1) to (III-10), wherein the composition for the inhibition or improvement of symptoms of ASD is an orally administered drug or a food or drink.

(IV) Method for Inhibiting or Improving Symptoms of ASD in Subject Having Symptoms of ASD (IV-1) A method for inhibiting or improving symptoms of ASD in a subject, the method comprising the step of administering at least one pyridoxamine compound selected from the group consisting of pyridoxamine and pharmaceutically acceptable salts thereof, or a preparation containing the at least one pyridoxamine compound to a subject having symptoms of ASD, preferably a subject diagnosed with ASD, wherein the "a subject" as used herein includes a human and a non-human mammal, and the phrase "a subject diagnosed with ASD" includes an ASD patient; the same applies hereinafter.

(IV-2) The method according to (IV-1), further comprising the step of administering at least one thiamine compound selected from the group consisting of thiamine, derivatives thereof, and pharmaceutically acceptable salts thereof to the subject having symptoms of ASD, preferably the subject diagnosed with ASD.

(IV-3) The method according to (IV-1) or (IV-2), wherein the symptom of ASD is a deficit in social communication and social interaction, and/or a restricted, repetitive pattern or stereotyped pattern of behavior, interests, or activities.

(IV-4) The method according to any one of (IV-1) to (IV-3), wherein the daily dose (or intake) of the at least one pyridoxamine compound is, on a pyridoxamine amount basis, 10 mg or more in the case of a food or drink, and 300 mg or more in the case of an orally administered drug.

(IV-5) The method according to any one of (III-2) to (IV-4), wherein the daily dose (or intake) of the at least one thiamine compound is 1 to 500 mg on a thiamine amount basis.

(IV-6) The method according to any one of (IV-2) to (IV-5), wherein the daily dose of (2) the at least one thiamine compound is 1 to 20 parts by weight, per 100 parts by weight of the daily dose of (1) the at least one pyridoxamine compound.

(IV-7) The method according to any one of (IV-2) to (IV-6), wherein (1) the at least one pyridoxamine compound and (2) the at least one thiamine compound are each packaged alone, or with a pharmaceutically acceptable carrier or additive in separate preparations; and the at least one pyridoxamine compound or the preparation containing the at least one pyridoxamine compound and the at least one thiamine compound or the preparation containing the at least one thiamine compound are administered to a subject at different times, simultaneously, or in parallel.

(IV-8) The method according to (IV-7), wherein the at least one pyridoxamine compound or the preparation containing the at least one pyridoxamine compound is administered to a subject before administration of the at least one thiamine compound or the preparation containing the at least one thiamine compound, or the at least one pyridoxamine compound or the preparation containing the at least one pyridoxamine compound is administered to a subject after administration of the at least one thiamine compound or the preparation containing the at least one thiamine compound.

(IV-9) The method according to any one of (IV-2) to (IV-8), wherein the at least one pyridoxamine compound and (2) the at least one thiamine compound are each packaged together with a pharmaceutically acceptable carrier or additive in the form of a combination drug prepared as a single preparation; and the at least one pyridoxamine compound or the preparation containing the at least one pyridoxamine compound and the at least one thiamine compound or the preparation containing the at least one thiamine compound are simultaneously administered to a subject.

(IV-10) The method according to any one of (IV-1) to (IV-9), wherein the preparation containing the at least one pyridoxamine compound and the preparation containing the at least one thiamine compound are an orally administered drug, or a food or drink.

Advantageous Effects of Invention

The composition according to the present invention improves the symptoms of ASD in a subject showing the symptoms of ASD. In particular, the composition according to the present invention improves the symptoms prescribed as DSM-5 diagnostic criteria A (deficits in social communication and social interaction) and/or DSM-5 diagnostic criteria B (restricted, repetitive patterns or stereotyped patterns of behavior, interests, or activities), which are characteristic symptoms of ASD. Additionally, the composition improves the symptoms of ASD, while preventing the onset of vitamin $B_1$ deficiency, which may develop when a high dose of a vitamin $B_6$ compound is administered.

BRIEF DESCRIPTION OF DRAWINGS

FIG. 1 illustrates an excerpt of ASD diagnostic criteria from "Diagnostic and Statistical Manual of Mental Disorders," fifth edition (DSM-5), prepared by the American Psychiatric Association.

FIG. 2 illustrates the relation between 58 diagnostic items in ABC-J (including subscales) and DSM-5 diagnostic criteria, and the relation between 58 diagnostic items in ABC-J, 57 diagnostic items in PARS-TR, and ADI-R algorithm classification.

FIG. 3 illustrates 57 assessment items of the revised version of the Pervasive Developmental Disorders Autism Society Rating Scale, PARS (PARS-TR).

FIG. 4 illustrates 43 items of the Japanese version of the Repetitive Behavior Scale—Revised (including 6 subscales), and the relation between these items and diagnostic criteria A and B in DSM-5.

FIG. 7 illustrates the results of scoring the symptoms of an ASD patient (case 3) based on ABC-J before and 8 weeks after the administration of a test drug. FIG. 7A illustrates the results of the total score of all 58 items of ABC-J in comparison, and FIG. 7B illustrates the results of the total score for every subscale of the 58 items of ABC-J in comparison.

FIG. 8 illustrates the results of scoring the symptoms of an ASD patient (case 3) based on RSB-R before and 8 weeks after the administration of a test drug. FIG. 8A illustrates the results of the total score of all 43 items of RSB-R in comparison, and FIG. 8B illustrates the results of the total score for every subscale of the 43 items of RSB-R in comparison.

FIG. 9 illustrates the results of scoring the symptoms of an ASD patient (case 4) based on ABC-J before and 8 weeks after the administration of a test drug. FIG. 9A illustrates the results of the total score of all 58 items of ABC-J in comparison, and FIG. 9B illustrates the results of the total score for each subscale item of the 58 items of ABC-J in comparison.

FIG. 10 illustrates the results of scoring the symptoms of an ASD patient (case 4) based on RSB-R before and 8 weeks after the administration of a test drug. FIG. 10A illustrates the results of the total score of all 43 items of RSB-R in comparison, and FIG. 10B illustrates the results of the total score for every subscale of the 43 items of RSB-R in comparison.

FIG. 12 illustrates the administration protocol of a pyridoxamine compound (pyridoxamine dihydrochloride: in the figure, "PM") and a thiamine compound (fursultiamine: in the figure, "VB1") for two test subjects (ID: Nos. 3 and 6), and also illustrates the vitamin B: ($VB_1$) level in whole blood as well as the pyridoxamine (PM) level, pyridoxal (PL) level, and pyridoxine (PN) level in serum of these patients measured over time. The star symbol indicates a time point at which Wernicke's encephalopathy was suspected, and the filled circle indicates a time point at which the symptoms of Wernicke's encephalopathy disappeared.

FIG. 13 illustrates changes in (A) the pyridoxamine (the unchanged substance) level and (B) the pyridoxal (PL) level in plasma (ng/mL) after the administration of a pyridoxamine compound (pyridoxamine dihydrochloride) to test subjects (6 subjects in each group, Δ: a group administered 300 mg/dose, ●: a group administered 600 mg/dose, and □: a group administered 900 mg/dose). The pyridoxamine compound was orally administered to the subjects at a time point of 0 hours, 6 hours, and 12 hours.

FIG. 14 illustrates changes in (A) the 4-pyridoxic acid (4-PA) level and (B) the pyridoxine (PN) level in plasma (ng/mL) after the administration of a pyridoxamine compound (pyridoxamine dihydrochloride) to test subjects (6 subjects in each group, Δ: a group administered 300 mg/dose, ●: a group administered 600 mg/dose, and □: a group administered 900 mg/dose). The pyridoxamine compound was orally administered to the subjects at a time point of 0 hours, 6 hours, and 12 hours.

FIG. 15A is a graph illustrating measurement results of a sample that was incubated for 1 hour, and FIG. 15B is a graph illustrating measurement results of a sample that was incubated for 16 hours. The upper chart of each FIGS. 15A and 15B illustrates the vitamin $B_1$ level in whole blood, and the lower chart illustrates the vitamin $B_1$ level (BL: baseline) in human whole blood before incubation and the vitamin $B_1$ level after incubation.

DESCRIPTION OF EMBODIMENTS

Figure 5:
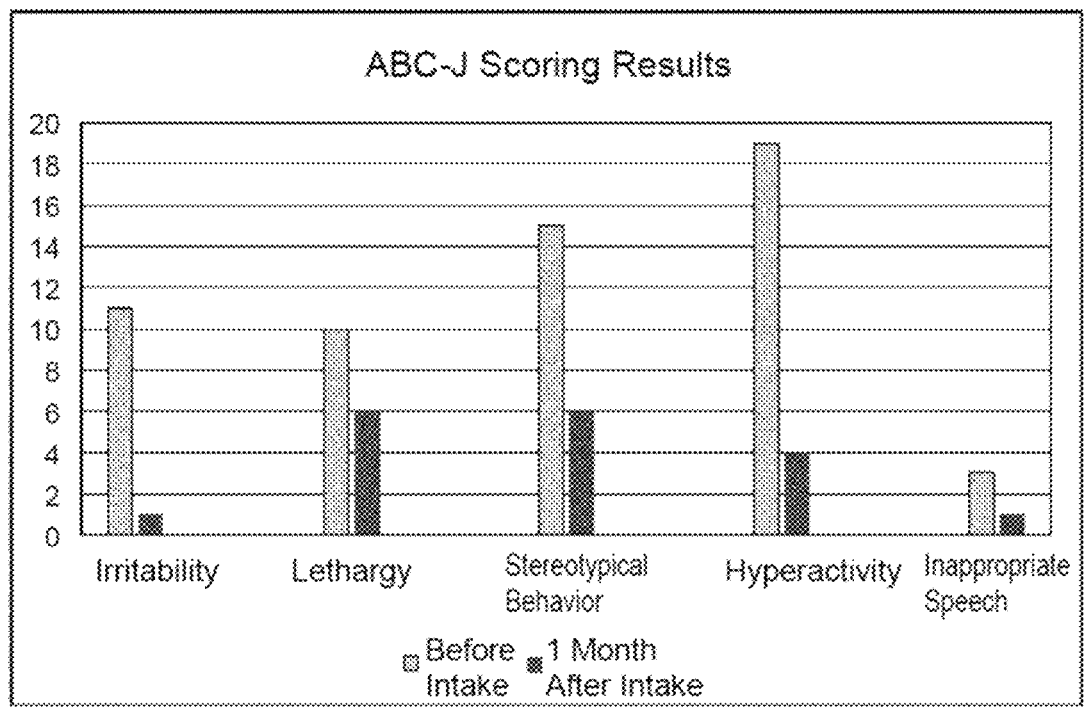
FIG. 5 illustrates the results of scoring the symptoms of an ASD patient (case 1) based on ABC-J before and 1 month after the administration of a test drug.

1. Composition for Inhibiting or Improving Symptoms of ASD

The composition for inhibiting or improving symptoms of ASD according to the present invention is used for inhibiting or improving the symptoms of ASD in a subject having symptoms of ASD.

The subject includes a human and a mammal other than a human, and the subject is preferably a human. The phrase "a subject having symptoms of ASD" includes a subject subclinically having symptoms of ASD, a subject suspected to have ASD (a suspected ASD patient), and a patient diagnosed with ASD (an ASD patient). The phrase "a subject having symptoms of ASD" also includes an ASD patient showing temporary improvement in symptoms of ASD, because the patient subclinically has symptoms of ASD, and there is a chance of recurrence. More specifically, although the composition of the present invention is typically used in a subject having symptoms of ASD (including an ASD patient) to improve the symptoms of ASD, the composition can also be used in a subject subclinically having symptoms of ASD and an ASD patient who has showed improvement in symptoms of ASD, in order to inhibit the symptoms of ASD (including recurrence) from developing or deteriorating. The subject is preferably an ASD patient, and the patient includes an ASD patient who has showed improvement in symptoms of ASD.

The term "improvement" as used in the present invention refers to alleviating or eliminating the developed symptoms of ASD. The term "inhibition" as used in the present invention refers to transiently or continually inhibiting the manifestation of symptoms of ASD. However, it is difficult to determine whether a condition has been improved or inhibited, and the term "improvement" as used in the present invention includes the meaning of "inhibition."

ASD is one type of neurodevelopmental syndrome (neurodevelopmental disorder). The terms (or definitions), disorder characteristics, and diagnostic criteria are detailed in the International Statistical Classification of Diseases and Related Health Problems (or simply, International Classification of Diseases (ICD)), tenth edition (Chapter 5, Mental and Behavioral Disorders) (hereinafter simply referred to as "ICD-10"), and the international diagnostic criteria guideline "DSM-5" (the Diagnostic and Statistical Manual of Mental Disorders, fifth edition) (hereinafter simply referred to as "DSM-5") published by the American Psychiatric Association in 2013. The previously mentioned NPT 1 is a Japanese version of DSM-5, which was supervised by the Japanese Society of Psychiatry and Neurology.

Of autistic disorder (autism), Asperger syndrome, pervasive developmental disorder not otherwise specified, childhood disintegrative disorder, and Rett disorder, which are all included in the pervasive developmental disorders (Pervasive Developmental Disorders: PDD) defined by ICD-10, the four conditions except for Rett disorder are collectively referred to as ASD (autism spectrum disorder), which is a newly established classification in DSM-5. Thus, DSM-5 has been used for diagnosis of ASD worldwide. The disclosures in this specification are also largely based on DSM-5, and the disclosures of the manual of DSM-5 are incorporated herein by reference.

FIG. 1 illustrates an excerpt of diagnostic criteria for ASD described in DSM-5. The diagnosis of ASD can be made based on "deficits in social communication and social interaction" (diagnostic criteria A) and "restricted, repetitive patterns or stereotyped patterns of behavior, interests, or activities" (diagnostic criteria B), which are the fundamental characteristics of ASD in the DSM-5 diagnostic criteria. However, the diagnosis of ASD based on DSM-5 varies, among the medical practitioners who make a diagnosis, regarding what category the symptoms fall under; and involves ambiguities because of the difficulty in making an accurate diagnosis. Thus, an ADI algorithm may also be used in combination to compensate for this difficulty, and to make a more rigorous assessment.

Methods for more specifically assessing or rating the symptoms of ASD include the Japanese version of the aberrant behavior checklist (Aberrant Behavior Checklist Community) (ABC-J, published by Jiho Inc. in 2006) (hereinafter simply referred to as "ABC-J"), the revised version of the Pervasive Developmental Disorders Autism Society Rating Scale (PARS) (hereinafter simply referred to as "PARS") (the revised version is hereinafter simply referred to as "PARS-TR"), and the Repetitive Behavior Scale—Revised (RSB-R) (hereinafter simply referred to as "RSB-R"). Thus, a subject can be assessed for whether they have symptoms of ASD; the severity of the symptoms; and whether they show improvement in symptoms, and the degree of improvement, based on at least one method selected from four diagnostic methods: ABC-J, PARS-TR, RSB-R, as well as the aforementioned DSM-5. In other words, whether the symptoms of ASD have been improved, or to what degree the symptoms have improved, may be determined based on one diagnostic method out of DSM-5, ABC-J, PARS-TR, and RSB-R; or two or more diagnostic methods in combination.

ABC-J is an aberrant behavior checklist available in Japan, which was made by translating and standardizing the revised version of the aberrant behavior checklist developed by American psychologists Aman M. G. and Singh N. N. as a rating scale for quantitatively assessing behavioral disorders associated with intellectual disability and developmental disorder. ABC-J is composed of 58 items that represent problematic behaviors, and a subject is assessed for each item on the following four-rating scale: there are no problems (0 points); the degree of problematic behavior is mild (1 point); the degree of problematic behavior is moderate (2 points); and the degree of problematic behavior is marked (3 points). These 58 items are classified into five subscales: I. Irritability (15 items); II. Lethargy (16 items); III. Stereotypical Behavior (7 items); IV. Hyperactivity (16 items); and V. Inappropriate Speech (4 items). Assessment can be made for each subscale (Ministry of Health, Labour and Welfare, Year 2012 Total Welfare Promotion Project for People with Disabilities, Guidelines for Support for and Assessment of Children with Developmental Disabilities, Asperger Society Japan (a specified non-profit organization), March 2013).

Figure 2:
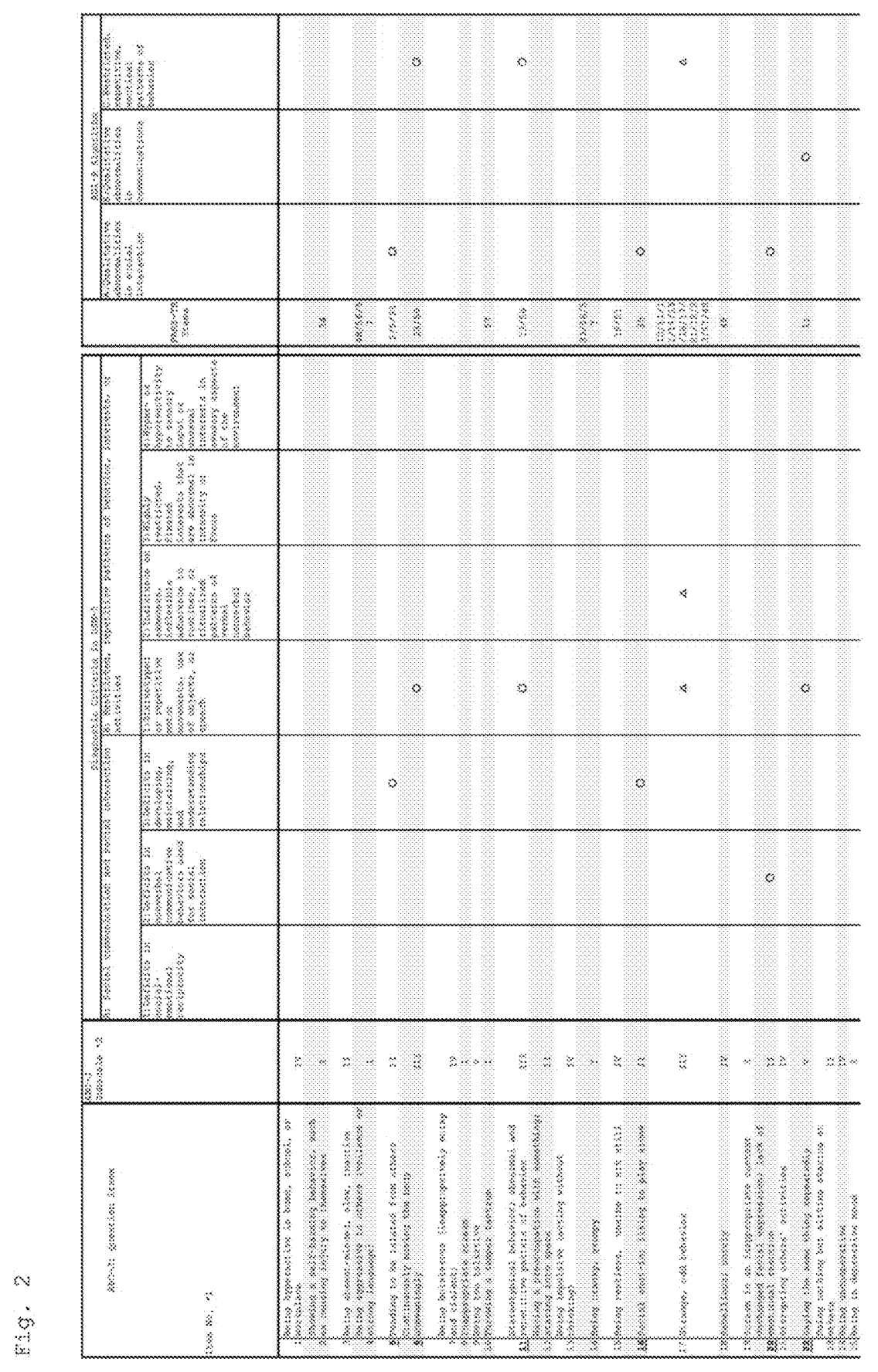

The details of the 58 checked items and subscales in ABC-J are shown in FIG. 2.

The subscales each include the following problematic behaviors.

(a) Subscale I: Irritability (15 Items): Items 2, 4, 8, 10, 14, 19, 25, 29, 34, 36, 41, 47, 50, 52, and 57

Subscale I includes problematic behaviors involving various forms of aggression and intense emotional ups and downs (frustration), such as violence and abusive language against others, destruction of objects, and self-harming behavior. Items related to "panic," such as crying out and throwing a temper tantrum, are included in this subscale.

(b) Subscale II: Lethargy (16 Items): Items 3, 5, 12, 16, 20, 23, 26, 30, 32, 37, 40, 42, 43, 53, 55, and 58

Unlike subscale I, subscale II includes inactivity, lack of activeness or response, isolation, and a tendency to avoid interpersonal exchanges (shut-in).

(c) Subscale III: Stereotypical Behavior (7 Items): Items 6, 11, 17, 27, 35, 45, and 49

Subscale III includes behaviors such as repeatedly and continuously moving the head, legs and arms, or the entire body meaninglessly, which is often observed in people with relatively severe intellectual disability or developmental disorder.

(d) Subscale IV: Hyperactivity (16 Items): Items 1, 7, 13, 15, 18, 21, 24, 28, 31, 38, 39, 44, 48, 51, 54, and 56

Subscale IV includes problems that are external problematic behaviors similar to those in subscale I, but that are not aggression directed to people or objects; examples include excessive activity, difficulty in focusing on things, and non-compliance or difficulty in following instructions.

(e) Subscale V: Inappropriate Speech (4 Items): Items 9, 22, 33, and 46

Subscale V includes items regarding inappropriate speech or production of sound that does not suit the social context; and repetitive words, such as talkativeness, speaking loudly, and repeatedly saying the same thing or a single word or phrase.

FIG. 2 illustrates 58 items (including subscales) of ABC-J, as well as the relation between these items and ASD diagnostic criteria A and B stated in DSM-5. Items of ABC-J that are related to diagnostic criteria A or B of DSM-5 are marked with ○ (the item number is underlined), and items of ABC-J that may be referred to for diagnostic criteria A and B of DSM-5 are marked with Δ (the item number is written in italic font). When focus is placed on diagnostic criteria A and B of DSM-5, assessment may be made with particular attention to items of ABC-J that are closely related to DSM-5.

PARS (Pervasive Developmental Disorder Autism Society Japan Rating Scale) is a scale composed of 57 items to determine the characteristics in pervasive developmental disorder (PDD) (which may hereinafter also simply be referred to as "PDD"), and to evaluate the support difficulty by interviewing the mothers of the subjects (or other rearer, if it is difficult to obtain information from the mother of a subject); PARS-TR is its revised version. The revised version contains revised wording of the commentary of question items, while maintaining the reliability and validity of the rating scale of the former PARS. On a side note, question items and rating in PARS-TR, PARS-TR items rated for each age group, a score calculation method, and an ASD characteristics test method are detailed in PARS-TR PARS Text Revision (written and edited by Hattatsu Shogai Shien no tameno Hyoka Kenkyu Kai [Study of the Assessment for Supporting Developmental Disorder], a general incorporated association, Spectrum Publishing Company), the disclosure of which is incorporated herein by reference.

FIG. 3 illustrates 57 rating items prescribed in PARS-TR. The rating items vary depending on the age group of targets for diagnosis (children before school age (early childhood), elementary school students (childhood), and junior high-school students or older subjects (early adolescence or adulthood)). Items 1 to 34 are directed to those in early childhood. Items 1 to 34 are intended to assess the peak in early childhood (assessment for most noticeable symptoms in early childhood) of all subjects (children before school age, elementary school students, and junior high-school students or older subjects), and also to assess the current condition of subjects in early childhood. Peak assessment and current condition assessment are performed for young children because, for example, clear autistic symptoms before the age of 4 years may be alleviated after age 5. Young children are not assessed by items 35 to 57. Elementary school students are assessed by items 1 to 34 for early childhood to determine the peak in early childhood, and items 21 to 53 for childhood to determine the current condition. Junior high-school students or older subjects are assessed by the 34 items for early childhood to determine the peak in early childhood, and items 25 to 57 for early adolescence or adulthood to determine the current condition. The specific evaluation method is described in detail in Example 2.

Although PARS-TR are diagnostic criteria for ASD prepared in Japan, the correspondence between PARS-TR and the ADI algorithm has been scientifically studied, and their compatibility has been confirmed. FIG. 2 is a table illustrating the relation between the 57 items of PARS-TR and the 58 items of ABC-J (items that ask a substantially similar question between PARS-TR and ABC-J), the relation between these items and DSM-5 (◯, △), and their classification for each ADI-R algorithm. For example, when focus is placed on diagnostic criteria of DSM-5, items closely related to DSM-5, among the 57 items of PARS-TR, can be selected for assessment.

RSB-R was prepared for the purpose of assessing, among the diagnostic criteria of DSM-5, diagnostic criteria B "restricted, repetitive patterns of behavior, interests, or activities" in more detail, and is a scale for assessing how many types of repetitive behaviors a child with ASD shows, and the severity of the problematic behaviors. RSB-R is composed of 6 subscales (I. Stereotypical Behavior, II. Self-Harming Behavior, III. Obsessive-Compulsive Behavior, IV. Ritualized Behavior, V. Insistence on Sameness, and VI. Circumscribed Interests) and 43 items. RSB-R (Japanese version) is a Japanese version of RBS-R, which is a rating scale used worldwide, and whose validity has already been verified (Inada et al., Research in Autism Spectrum Disorders, Vol. 15-16, July 2015, pp. 60-68; Inada et al., Study on reliability and validity of the Japanese version of Repetitive Behaviors Scale—Revised (RBS-R), The Japanese Journal of Developmental Psychology, 2012, Vol. 23, No. 2, pp. 123-133). FIG. 4 illustrates 43 items of RSB-R (including 6 subscales), and the relation between the 43 items of RSB-R and diagnostic criteria A and B of DSM-5.

A subject targeted in the present invention is one diagnosed as having symptoms of ASD by one of the following diagnostic methods: DSM-5, ABC-J, PARS-TR, and RSB-R described above. The subject is preferably one having symptoms of ASD that is classified into any of items (1) to (3) under diagnostic criteria A, and items (1) to (4) under diagnostic criteria B of DSM-5, which characteristically describe the symptoms of ASD, when the subject is diagnosed using any of these methods (i.e., DSM-5, ABC-J, PARS-TR, and RSB-R). The age (early childhood: 1 year after birth to before school age; childhood: elementary school students at 6 to 12 years of age; early adolescence or adulthood), gender, and body weight of the subject are not particularly limited. The age group is preferably those in childhood, early adolescence, or adulthood, and more preferably those in early adolescence or adulthood.

1-1. Composition for Inhibiting or Improving Symptoms of ASD Containing Pyridoxamine Compound as Active Substance The composition for inhibiting or improving symptoms of ASD of the present invention contains at least one pyridoxamine compound selected from the group consisting of pyridoxamine and pharmaceutically acceptable salts thereof as an active substance.

The term "pyridoxamine compound" as used in the present invention refers to at least one member selected from the group consisting of pyridoxamine (IUPAC name: 4-(aminomethyl)-5-(hydroxymethyl)-2-methylpyridin-3-ol) and pharmaceutically acceptable salts thereof. These may be used singly, or in any combination of two or more.

The pharmaceutically acceptable salts are not particularly limited, and include acid addition salts with inorganic acids, such as hydrochloric acid, hydrobromic acid, hydroiodic acid, sulfuric acid, nitric acid, and phosphoric acid; acid addition salts with organic acids, such as formic acid, acetic acid, propionic acid, oxalic acid, malonic acid, succinic acid, fumaric acid, maleic acid, lactic acid, malic acid, tartaric acid, citric acid, methanesulfonic acid, ethane sulfonic acid, aspartic acid, and glutamic acid; salts with metals, such as sodium, potassium (alkali metals), magnesium, calcium (alkaline-earth metals), and aluminum; salts with organic bases, such as methyl amine, ethyl amine, ethanol amine, lysine, and ornithine; and ammonium salts. The pharmaceutically acceptable salts are preferably acid addition salts with hydrochloric acid; and salts with metals such as sodium, potassium, magnesium, calcium, or aluminum, and more preferably pyridoxamine dihydrochloride.

The daily dose of the at least one pyridoxamine compound varies depending on whether the administered composition for inhibiting or improving symptoms of ASD is a pharmaceutical composition, or a food or drink composition.

For example, when the composition for inhibiting or improving symptoms of ASD of the present invention is an orally administered drug, the daily dose is 300 mg/day or more on a pyridoxamine basis. More specifically, the minimum daily dose of the at least one pyridoxamine compound is 300, 400, 500, 600, 700, or 800 mg on a pyridoxamine basis, and a more preferable minimum dose is suitably selected from this range. The minimum daily dose (mg/day) is 5, 6.7, 8.3, 10, or 13.3 mg/kg/day, if converted on a body weight basis (1 kg) with the assumption that the body weight is 60 kg. The maximum daily dose of the at least one pyridoxamine compound is 2000, 3000, 4000, 5000, or 10000 mg on a pyridoxamine basis, and a more preferable maximum dose can be suitably selected from this range. If this is converted on a body weight basis (1 kg) with the assumption that the body weight is 60 kg, the maximum daily dose is 33.3, 50.0, 66.7, 83.3, or 166.7 mg/kg/day.

When the composition for inhibiting or improving symptoms of ASD of the present invention is a food or drink, the daily dose of the at least one pyridoxamine compound is, for example, 10 mg/day or more on a pyridoxamine basis. The intake of pyridoxamine that is effective in inhibiting or improving symptoms of ASD through a food or drink is preferably more than about 0.5 to 1.4 mg/day, which is a daily intake of vitamin $B_6$ (see the report in Dietary Reference Intakes for Japanese (2015) Design Committee (Ministry of Health, Labour and Welfare in Japan), which recognizes the intake of vitamin $B_6$ as the total intake of pyridoxamine), and should be at least 2 mg/day or more. The effect in improving symptoms is more likely to become greater, as the pyridoxamine intake is increased. Thus, it is also effective to increase the minimum dose to 10, 20, 30, 40, 50, 60, or 100 mg/day. The upper limit is not necessarily clearly determined, and may be set at, for example 60, 80, 100, 150, 200, 250, or 300 mg/day. The upper limit may be determined, for example, to keep it to the minimum within the range in which the effect clearly appears, or within the range restricted in legislation, if any.

When the daily dose of the at least one pyridoxamine compound is 300 mg or more as described above, the vitamin $B_1$ level in the body decreases, which is likely to cause the development of side effects including vitamin $B_1$ deficiency such as Wernicke's encephalopathy. This is particularly noticeable in those with low body weight, such as elderly people and small children. Even people who are not classified as those with low body weight become more prone to vitamin $B_1$ deficiency, as the daily dose of the at least one pyridoxamine compound is increased, such as 300 mg or more, 400 mg or more, 500 mg or more, 600 mg or more, 600 mg or more, 700 mg or more, and 800 mg or more.

The starting day and ending day of administration (ingestion) of the composition for inhibiting or improving symptoms of ASD may be suitably determined depending on the day of the onset of the symptom of ASD and the lasting period of the symptoms in a subject having the symptoms of ASD (or an ASD patient).

The administration (ingestion) of the composition for inhibiting or improving symptoms of ASD may be performed once daily at a dose as described above. A subject having intense ASD symptoms may be administered (ingest) the composition twice a day (morning and evening) or 3 times a day (morning, afternoon, evening) at a daily dose as described above. The administration (ingestion) of the composition for inhibiting or improving symptoms of ASD may be performed every day or once every few days, e.g., every other day; but is preferably performed every day. The administration (ingestion) time is not particularly limited, and is, for example, after meal or before bedtime.

The composition for inhibiting or improving symptoms of ASD is preferably administered repeatedly. When the daily dose of the at least one pyridoxamine compound is 300 mg or more, the subject may be provided with a drug holiday from the end of one dosing period to the next dosing period to prevent vitamin $B_1$ deficiency.

The composition for inhibiting or improving symptoms of ASD may be prepared into a form of preparation by combining the at least one pyridoxamine compound with a suitable carrier or additive. The preparation as used herein includes not only preparations for medicinal use (pharmaceutical products), but also preparations for use in foods and drinks (food and drink products). Examples of the carrier and additive for use in preparing the composition in these preparation forms include a range of those widely used in typical medicinal agents and foods and drinks (e.g., supplements), depending on the dosage form, such as excipients, binders, disintegrants, lubricants, colorants, flavoring agents, smell-masking agents, and surfactants.

When the composition for inhibiting or improving symptoms of ASD is an orally administered drug or a food or drink, the dosage form is not particularly limited. Examples include tablets, powdered drugs, granules, capsules (including hard capsules and soft capsules), fluid medicines, pills, suspension agents, and emulsions. When the composition for inhibiting or improving symptoms of ASD is a parenterally administered pharmaceutical composition, examples include injectable drugs, intravenous drips, suppositories, nasal drops, and pulmonary-administered agents. The composition of the present invention may be either an oral composition or a parenteral composition, and is preferably an oral composition (orally administered drugs, and food and drink).

When the composition for inhibiting or improving symptoms of ASD is an orally administered solid composition (e.g., tablets, powdered drugs, granules, pills, or capsules), the following, for example, may be used as carriers in preparing the composition: excipients, such as lactose, sucrose, sodium chloride, glucose, urea, starch, calcium carbonate, kaolin, crystalline cellulose, silicic acid, methylcellulose, glycerin, sodium alginate, and gum arabic; binders, such as simple syrup, dextrose solutions, starch solutions, gelatin solutions, polyvinyl alcohol, polyvinyl ether, polyvinyl pyrrolidone, carboxy methylcellulose, shellac, methyl cellulose, ethyl cellulose, water, ethanol, and potassium phosphate; disintegrants, such as dry starch, sodium alginate, powdered agar, powdered laminaran, sodium hydrogen carbonate, calcium carbonate, polyoxyethylene sorbitan fatty acid esters, sodium lauryl sulfate, monoglyceride stearate, starch, and lactose; disintegration inhibitors, such as sucrose, stearic acid, cocoa butter, and hydrogenated oil; absorption promoters, such as sodium lauryl sulfate; moisturizing agents, such as glycerin, and starch; adsorbents, such as starch, lactose, kaolin, bentonite, and colloidal silica; and lubricants, such as purified talc, salts of stearic acid, powdered boric acid, and polyethylene glycol. Additionally, tablets may be formed into tablets with typical coating where necessary, such as sugar-coated tablets, tablets wrapped with gelatin, enteric-coated tablets, film-coated tablets, double-compressed tablets, and multi-layered tablets.

When the composition for inhibiting or improving symptoms of ASD is an orally administered solid composition in the form of pills, the following, for example, may be used as carriers in preparing the composition: excipients, such as glucose, lactose, starch, cacao oil, hydrogenated vegetable oil, kaolin, and talc; binders, such as powdered gum arabic, powdered tragacanth, and gelatin; and disintegrants, such as laminaran and agar.

When the composition for inhibiting or improving symptoms of ASD is an orally administered solid composition in the form of capsules, the capsules are prepared by mixing the active substance with various carriers listed above as examples, and packed in or wrapped with a hard capsule base material, a soft capsule base material, or the like.

When the composition for inhibiting or improving symptoms of ASD is a fluid medicine, the medicine may be an aqueous or oil-based suspension, a solution, a syrup, or an elixir. The fluid medicine is prepared using typical additives in accordance with a standard method.

When the composition for inhibiting or improving symptoms of ASD is an injectable drug, the following, for example, may be used as carriers in preparing the drug: diluents, such as water, ethyl alcohol, macrogol, propylene glycol, ethoxylated isostearyl alcohol, polyoxylated isostearyl alcohol, and polyoxyethylene sorbitan fatty acid esters; pH adjusters, such as sodium citrate, sodium acetate, and sodium phosphate; buffers, such as dipotassium phosphate, trisodium phosphate, sodium hydrogen phosphate, and sodium citrate; stabilizers, such as sodium pyrosulfite, EDTA, thioglycolic acid, and thiolactic acid; and saccharides, such as mannitol, inositol, maltose, sucrose, and lactose, for shape-formers when the composition is freeze-dried. In this case, a sufficient amount of glucose or glycerin to prepare an isotonic solution may be added to the drug; a typical solubilizing agent, a soothing agent, a local anesthetic, etc., may also be added to the drug. Subcutaneously, intramuscularly, or intravenously injected drugs can be prepared by adding these carriers in accordance with a standard method.

When the composition for inhibiting or improving symptoms of ASD is an intravenous drip, such a drip can be prepared by dissolving the at least one pyridoxamine compound to be administered in an isotonic electrolyte solution based on physiological saline, Ringer's solution, or the like.

1-2. Composition for Inhibiting or Improving Symptoms of ASD in the Form of Combination of Pyridoxamine Compound with Thiamine Compound The composition for inhibiting or improving symptoms of ASD of the present invention, as described above, contains a pyridoxamine compound as an active substance. The composition may also be in the form of a combination of the pyridoxamine compound with at least one thiamine compound selected from the group consisting of thiamine, derivatives thereof, and pharmaceutically acceptable salts thereof. More specifically, the composition for inhibiting or improving symptoms of ASD of the present invention may be a combination of (1) at least one pyridoxamine compound selected from the group consisting of pyridoxamine and pharmaceutically acceptable salts thereof with (2) at least one thiamine compound selected from the group consisting of thiamine, derivatives thereof, and pharmaceutically acceptable salts thereof; and the combination is usable for inhibiting or improving the symptoms of ASD in a subject having symptoms of ASD.

The "thiamine compound" as used in the present invention refers to at least one member selected from the group consisting of thiamine, derivatives thereof, and pharmaceutically acceptable salts thereof. Thus, these may be used singly, or in any combination of two or more.

The thiamine derivatives may be disulfide-type derivatives, acyl-type derivatives, or mixtures thereof. Examples of thiamine derivatives include bisthiamine, thiamine disulfide, thiamine dicetylsulfate, benfotiamine, prosultiamine, fursultiamine, bisbentiamine, cycotiamine, octotiamine, allithiamine, prosultiamine, thiamine tetrahydrofurfuryl disulfide, dicethiamine, bisbuthiamine, bisibuthiamine, thiamine monophosphate disulfide, thiamin pyrophosphate, cycotiamine, and thiamine ethyldisulfide. The thiamine derivative is preferably at least one member selected from the group consisting of octotiamine, prosultiamine, fursultiamine, bisbentiamine, benfotiamine, cocarboxylase, and thiamine disulfide, and more preferably at least one member selected from the group consisting of octotiamine, prosultiamine, and fursultiamine. The thiamine derivative is still more preferably fursultiamine; however, the thiamine derivative is not limited to these derivatives.

The pharmaceutically acceptable salts of thiamine or derivatives of thiamine are not particularly limited. Examples include acid addition salts with inorganic acids, such as hydrochloric acid, hydrobromic acid, hydroiodic acid, sulfuric acid, nitric acid, and phosphoric acid; acid addition salts with organic acids, such as formic acid, acetic acid, propionic acid, oxalic acid, malonic acid, succinic acid, fumaric acid, maleic acid, lactic acid, malic acid, tartaric acid, citric acid, methanesulfonic acid, ethane sulfonic acid, aspartic acid, and glutamic acid; salts with metals, such as sodium, potassium (alkali metals), magnesium, calcium (alkaline-earth metals), and aluminum; salts with organic bases, such as methyl amine, ethyl amine, ethanol amine, lysine, and ornithine; and ammonium salts. The pharmaceutically acceptable salts are preferably acid addition salts with hydrochloric acid; salts with metals, such as sodium, potassium, magnesium, calcium, and aluminum, and most preferably acid addition salts with inorganic acids, such as hydrochloride and nitrate.

The at least one thiamine compound is preferably at least one member selected from the group consisting of octotiamine, prosultiamine, fursultiamine, bisbentiamine, benfotiamine, cocarboxylase, thiamine disulfide, salts thereof, thiamine chloride hydrochloride, thiamine nitrate, and dicethiamine hydrochloride; more preferably at least one member selected from the group consisting of octotiamine, prosultiamine, fursultiamine, and salts thereof; and still more preferably fursultiamine, and salts thereof (e.g., fursultiamine hydrochloride).

The combination of at least one pyridoxamine compound with at least one thiamine compound that is the target of the composition for inhibiting or improving symptoms of ASD of the present invention include the following aspects:

(i) the aspect in which the at least one pyridoxamine compound and the at least one thiamine compound are contained in a single preparation, with the two compounds being mixed (combination drug);

(ii) the aspect in which the at least one pyridoxamine compound (single drug) or a preparation containing the at least one pyridoxamine compound and the at least one thiamine compound (single drug) or a preparation containing the at least one thiamine compound are each packaged as separate preparations, and both are sold as a combination (kit);

(iii) the aspect in which the at least one pyridoxamine compound (single drug) or a preparation containing the at least one pyridoxamine compound and the at least one thiamine compound (single drug) or a preparation containing the at least one thiamine compound are separate preparations, and these are combined and sold in a single package; or (iv) the aspect in which the at least one pyridoxamine compound (single drug) or a preparation containing the at least one pyridoxamine compound and the at least one thiamine compound (single drug) or a preparation containing the at least one thiamine compound are each packaged as separate preparations, and they are present in the market through different distribution routes and combined when used.

Specifically, it is sufficient if "the combination of at least one pyridoxamine compound with at least one thiamine compound" targeted by the present invention is the aspect in which the at least one pyridoxamine compound or a preparation containing the at least one pyridoxamine compound is administered to (ingested by) a subject at different times, simultaneously, or in parallel with the administration (ingestion) of the at least one thiamine compound or a preparation containing the at least one thiamine compound and the form of the at least one pyridoxamine compound and the form of the at least one thiamine compound in distribution (including in sales) does not particularly matter. This aspect also includes an aspect in which the at least one pyridoxamine compound or a preparation containing the at least one pyridoxamine compound is administered to (ingested by) a subject before the administration (ingestion) of the at least one thiamine compound or a preparation containing the at least one thiamine compound, and an aspect in which the at least one pyridoxamine compound or a preparation containing the at least one pyridoxamine compound (ingestion) is administered to (ingested by) a subject after the administration (ingestion) of the at least one thiamine compound or a preparation containing the at least one thiamine compound.

The "preparation containing the at least one pyridoxamine compound" as used here refers to a preparation prepared by combining the at least one pyridoxamine compound with other components. The "preparation containing the at least one thiamine compound" refers to a preparation prepared by combining the at least one thiamine compound with other components. These preparations are distinguished from a preparation composed of the at least one pyridoxamine compound (single drug), and a preparation composed of the at least one thiamine compound (single drug). Other components include the carriers and additives described in section 1-1 above, and these preparations are also prepared as described in section 1-1.

The daily dose of the at least one pyridoxamine compound may be determined on a pyridoxamine amount basis in the same manner as with the composition for inhibiting or improving symptoms of ASD described in section 1-1 above. The starting day, ending day, and one dosing period of the administration of the at least one pyridoxamine compound may also be determined in the same manner as with the composition for inhibiting or improving symptoms of ASD described in section 1-1.

The composition for inhibiting or improving symptoms of ASD in the aspect of a combination of the at least one pyridoxamine compound and the at least one thiamine compound may be administered every day, because the development of vitamin $B_1$ deficiency caused by the intake of the at least one pyridoxamine compound can be prevented by the intake of the at least one thiamine compound.

The daily dose of the at least one thiamine compound is not particularly limited, and the thiamine content of commercially distributed vitamin preparations may be applied. For example, the minimum daily dose of the at least one thiamine compound may be 1, 2, 5, or 10 mg or more on a thiamine amount basis, and a more preferable minimum dose may be suitably selected from this range. The maximum dose is 50, 100, 300, or 500 mg, and a more preferable maximum dose may be suitably selected from this range.

The dose of the at least one thiamine compound per 100 parts by weight of the dose of the at least one pyridoxamine compound is 1 to 20 parts by weight, and the lower limit per 100 parts by weight of the dose of the at least one pyridoxamine compound is preferably 1, 1.5, or 3 parts by weight. The upper limit is preferably 10, 15, or 20 parts by weight.

The at least one thiamine compound may be administered simultaneously with the administration (ingestion) of the at least one pyridoxamine compound, or at a different time. The time period for administration (dosing period) of the at least one thiamine compound may be the same as the time period for the administration (dosing period) of the at least one pyridoxamine compound, or the dosing period of the at least one thiamine compound may be pushed before or after the dosing period of the at least one pyridoxamine compound. The starting day and ending day of the administration of the at least one thiamine compound may suitably be determined according to the dosing period of the at least one pyridoxamine compound.

The at least one thiamine compound may be administered once daily at the dose described above; the at least one thiamine compound may also be administered twice (morning and evening) a day or three times (morning, afternoon, and evening) a day at the dose described above, depending on the dose of the at least one pyridoxamine compound. A composition that also contains the at least one thiamine compound may be administered every day or every few days, such as every other day, and preferably administered every day.

The at least one pyridoxamine compound and the at least one thiamine compound may be administered as individual single drugs or as preparations containing other components in combination (a preparation containing the at least one pyridoxamine compound and a preparation containing the at least one thiamine compound), for example, perorally, intramuscularly, subcutaneously, and/or intravascularly. Preferably, a preparation containing the at least one pyridoxamine compound and a preparation containing the at least one thiamine compound are both administered perorally.

The preparation containing the at least one pyridoxamine compound and/or the preparation containing the at least one thiamine compound can be prepared by combining the at least one pyridoxamine compound and/or the at least one thiamine compound with suitable carriers or additives used in preparations. The carriers and additives used in preparations may be those listed in section 1-1 above. These preparations may also be prepared in accordance with the preparation method described in section 1-1 above.

2. Method for Inhibiting or Improving Symptoms of ASD

The method for inhibiting or improving symptoms of ASD according to the present invention can be performed by administering (feeding) the composition for inhibiting or improving symptoms of ASD described in sections 1-1 or 1-2 above to a subject having symptoms of ASD.

The symptom of ASD and the subject having symptoms of ASD as used herein are as described in section 1 above, and the disclosure is incorporated here by reference. The subject is preferably an individual in early childhood, childhood, or early adolescence/adulthood who has symptoms of ASD that meets any of items (1) to (3) under diagnostic criteria A and items (1) to (4) under diagnostic criteria B of DSM-5, when assessed by every method of DSM-5, ABC-J, PARS-TR, and RSB-R. The subject is more preferably an individual who has symptoms of ASD that meets items (1) to (4) under diagnostic criteria B of DSM-5, and still more preferably an individual who has symptoms of ASD that meets items (1) and/or (4) under diagnostic criteria B of DSM-5. The age group is not limited, but is preferably an individual in childhood or early adolescence/adulthood, and more preferably an individual in early adolescence or adulthood.

The formulation, the administration method, and the dosing period of the composition for inhibiting or improving symptoms of ASD to be administered are as described in sections 1-1 and 1-2 above, and the disclosures are incorporated herein by reference.

When the composition for inhibiting or improving symptoms of ASD is a combination of (1) the at least one pyridoxamine compound and (2) the at least one thiamine compound that are each packaged alone or with a pharmaceutically acceptable carrier or additive in separate preparations, the pyridoxamine compound or a preparation containing the at least one pyridoxamine compound, and the at least one thiamine compound or a preparation containing the at least one thiamine compound are administered to (ingested by) a subject at different times, simultaneously, or in parallel. When both are administered at different times, the administration timing is not particularly limited. The at least one pyridoxamine compound or a preparation containing the at least one pyridoxamine compound may be administered before the administration of the at least one thiamine compound or a preparation containing the at least one thiamine compound, or the at least one pyridoxamine compound or a preparation containing the at least one pyridoxamine compound may be administered after the administration of the at least one thiamine compound or a preparation containing the at least one thiamine compound.

EXAMPLES

The following describes the present invention with reference to Reference Experimental Examples and Experimental Examples in detail. However, the present invention is not limited to these Examples.

Example 1: Administration of Pyridoxamine Compound to ASD Patient (Case 1)

A pyridoxamine compound was administered to a test subject diagnosed with ASD (ASD patient), and the effect in improving symptoms of ASD brought about by the administration was examined in an exploratory manner.
1. Method
An ASD patient (female, 29 years old, body weight: 54 kg) took a test drug orally every day for 1 month, and her symptoms of ASD were assessed by ABC-J as a diagnostic method before taking the drug (before the start of administration) and 1 month after taking the drug (1 month after the start of administration).
Test Drug
Pyridoxamine Dihydrochloride: twice a day after breakfast and dinner, every day, 300 mg/dose (600 mg/day)
Vitamin B$_1$ (Fursultiamine): one time a day after breakfast every day when taking pyridoxamine dihydrochloride, 25 mg/dose (25 mg/day)
Diagnostic Method
The symptoms of ASD of the test subject were assessed by a family member who lives with the subject and has professional expertise on ASD with ABC-J based on the behaviors of the subject.
2. Results
Table 1 and FIG. 5 show the results that are scores of ABC-J of the test subject summarized for every subscale in before and after taking the drug.

TABLE 1

| Irritability | | Lethargy | | Stereotypical Behavior | | Hyperactivity | | Inappropriate Speech | |
|---|---|---|---|---|---|---|---|---|---|
| ABC-J: Before the Start of Administration | | | | | | | | | |
| 2 | 0 | 3 | 0 | 6 | 3 | 1 | 2 | 9 | 0 |
| 4 | 0 | 5 | 0 | 11 | 3 | 7 | 2 | 22 | 2 |
| 8 | 1 | 12 | 1 | 17 | 1 | 13 | 0 | 33 | 0 |
| 10 | 2 | 16 | 0 | 27 | 2 | 15 | 2 | 46 | 1 |
| 14 | 2 | 20 | 1 | 35 | 2 | 18 | 1 | | |
| 19 | 1 | 23 | 2 | 45 | 2 | 21 | 1 | | |
| 25 | 1 | 26 | 1 | 49 | 2 | 24 | 1 | | |
| 29 | 1 | 30 | 1 | | | 28 | 1 | | |
| 34 | 0 | 32 | 0 | | | 31 | 1 | | |
| 36 | 1 | 37 | 1 | | | 38 | 2 | | |
| 41 | 1 | 40 | 1 | | | 39 | 2 | | |
| 47 | 0 | 42 | 0 | | | 44 | 2 | | |
| 50 | 0 | 43 | 1 | | | 48 | 1 | | |
| 52 | 0 | 53 | 0 | | | 51 | 1 | | |
| 57 | 1 | 55 | 0 | | | 54 | 0 | | |
| | | 58 | 1 | | | 56 | 0 | | |
| 11 | | 10 | | 15 | | 19 | | 3 | |
| ABC-J: 1 Month After the Start of Administration | | | | | | | | | |
| 2 | 0 | 3 | 0 | 6 | 1 | 1 | 1 | 9 | 0 |
| 4 | 1 | 5 | 0 | 11 | 1 | 7 | 0 | 22 | 1 |
| 8 | 0 | 12 | 1 | 17 | 0 | 13 | 0 | 33 | 0 |
| 10 | 0 | 16 | 0 | 27 | 1 | 15 | 1 | 46 | 0 |
| 14 | 0 | 20 | 1 | 35 | 1 | 18 | 0 | | |
| 19 | 0 | 23 | 1 | 45 | 1 | 21 | 0 | | |
| 25 | 0 | 26 | 0 | 49 | 1 | 24 | 0 | | |
| 29 | 0 | 30 | 0 | | | 28 | 0 | | |
| 34 | 0 | 32 | 1 | | | 31 | 0 | | |
| 36 | 0 | 37 | 0 | | | 38 | 1 | | |
| 41 | 0 | 40 | 1 | | | 39 | 0 | | |
| 47 | 0 | 42 | 0 | | | 44 | 0 | | |
| 50 | 0 | 43 | 0 | | | 48 | 1 | | |
| 52 | 0 | 53 | 0 | | | 51 | 0 | | |
| 57 | 0 | 55 | 0 | | | 54 | 0 | | |
| | | 58 | 1 | | | 56 | 0 | | |
| 1 | | 6 | | 6 | | 4 | | 1 | |

As shown in Table 1 and FIG. 5, compared with the scores before taking the drug, significant improvement in symptoms was observed across the entire 5 subscales I to V (Irritability, Lethargy, Stereotypical Behavior, Hyperactivity, and Inappropriate Speech). Improvement was particularly noticeable in symptoms under subscale III (Stereotypical Behavior) (in particular, symptoms stated in items 6, 11, 17, 27, 35, 45, and 49) and symptoms under subscale II (Lethargy) (in particular, symptoms stated in items 30, 37, and 43), which are closely related to diagnostic criteria of DSM-5 (mainly A and B) and are characteristic symptoms in ASD. Additionally, taking the test drug for 1 month led to improvement to the point of "0=no problem" in the symptoms stated in items 8, 10, 14, 19, 25, 29, 36, 41 and 57 under subscale I (Irritability); the symptoms stated in items 7, 18, 21, 24, 28, 31, 39, 44, and 51 under subscale IV (Hyperactivity); and the symptoms stated in item 46 under subscale V (Inappropriate Speech).

Example 2: Effect of Administration of Pyridoxamine Compound to ASD Patient (Case 2)

A pyridoxamine compound was administered to an ASD patient, who is not the test subject in Example 1, and the effect in improving symptoms of ASD brought about by the administration was examined in an exploratory manner.
1. Method
A patient diagnosed with ASD (male, 27 years old, body weight: 76 kg) orally took the test drug detailed below every day over 17 days, and the symptoms of ASD were assessed by the diagnostic method described below before taking the drug (before the start of administration) and 17 days after taking the drug (17 days after the start of administration).
Test Drug
Pyridoxamine Dihydrochloride: twice a day after breakfast and dinner, every day, 300 mg/dose (600 mg/day)

Vitamin B$_1$ (Fursultiamine): one time a day after breakfast every day when taking pyridoxamine dihydrochloride, 25 mg/dose (25 mg/day)

Diagnosis Method

The symptoms of the test subject were assessed in accordance with diagnostic criteria of ABC-J and diagnostic criteria in line with PARS-TR before taking the drug and 17 days after taking the drug, by the same medical specialist.

Assessment by PARS-TR is performed by questioning the mother or someone else regarding the severity of symptoms concerning development and behaviors described in rating items in terms of "assessment of the peak in early childhood" and "assessment of the current condition," and the answer was classified into the following 3 levels and assessed: "0=none (no symptoms asked were observed/no)," "1=somewhat noticeable (symptoms asked were sometimes (somewhat) observed/yes)," and "2=noticeable (symptoms asked were often (quite) observed/yes)." The PARS-TR score is a value determined by simply summing up the assessment score of each item, excluding items that cannot be assessed. Based on this PARS-TR score, PDD (pervasive developmental disorder) characteristics are determined as shown in Table 2 below. Specifically, the cutoff value at which the subject is diagnosed with PDD is score 9 in early childhood, score 13 in childhood, and score 20 in early adolescence or adulthood.

TABLE 2

|  | PDD is less likely | PDD is strongly suggested |
|---|---|---|
| Peak or in early childhood | 8 or less | 9 or more |
| Current score in early childhood | 8 or less | 9 or more |
| Current score in childhood | 12 or less | 13 or more |
| Current score in adolescence or adulthood | 19 or less | 20 or more |

Because the target of this test is an adult, items 25 to 57 of PARS-TR were used for questions, and assessment was performed before and 17 days after taking the drug. The total scores were compared.

2. Results

Figure 6:
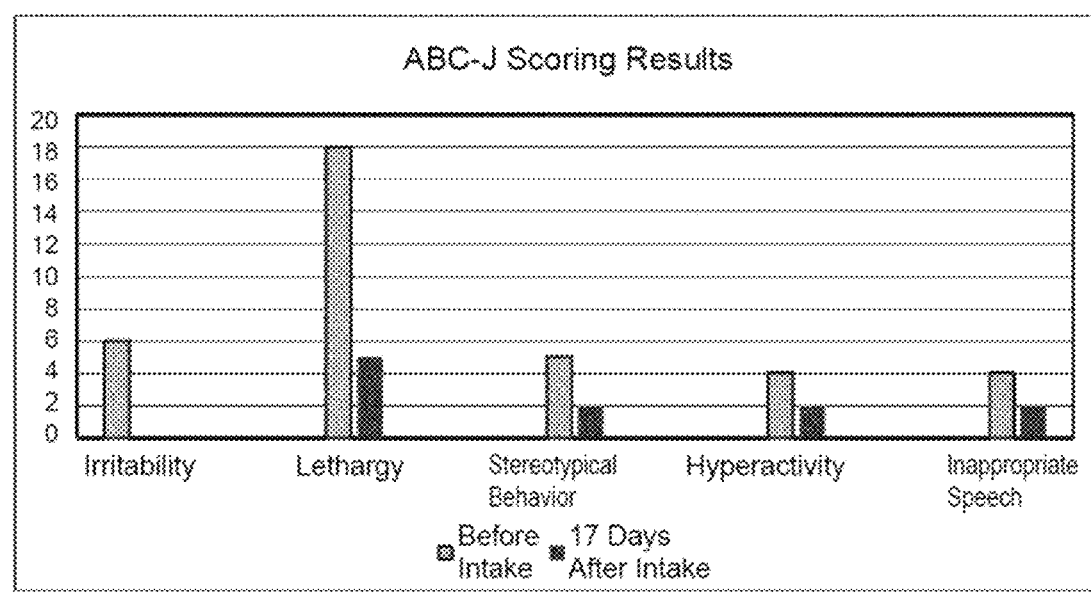
FIG. 6 illustrates the results of scoring the symptoms of an ASD patient (case 2) based on ABC-J before and 17 days after the administration of a test drug.

Table 3 and FIG. 6 show ABC-J scores before and 17 days after the subject took the drug, summarized for every subscale. Table 4 shows items 25 to 57 of PARS-TR, and a comparison in scores for each item and the sum of the scores between before and 17 days after the drug intake.

TABLE 3

| Irritability | | Lethargy | | Stereotypical Behavior | | Hyperactivity | | Inappropriate Speech | |
|---|---|---|---|---|---|---|---|---|---|
| ABC-J: Before the Start of Administration | | | | | | | | | |
| 2 | 0 | 3 | 2 | 6 | 2 | 1 | 1 | 9 | 0 |
| 4 | 1 | 5 | 2 | 11 | 0 | 7 | 0 | 22 | 2 |
| 8 | 0 | 12 | 1 | 17 | 0 | 13 | 0 | 33 | 0 |
| 10 | 1 | 16 | 2 | 27 | 0 | 15 | 1 | 46 | 2 |
| 14 | 2 | 20 | 1 | 35 | 1 | 18 | 0 | | |
| 19 | 0 | 23 | 1 | 45 | 2 | 21 | 1 | | |
| 25 | 2 | 26 | 1 | 49 | 0 | 24 | 1 | | |
| 29 | 0 | 30 | 1 | | | 28 | 0 | | |
| 34 | 0 | 32 | 0 | | | 31 | 0 | | |
| 36 | 0 | 37 | 1 | | | 38 | 0 | | |
| 41 | 0 | 40 | 1 | | | 39 | 0 | | |
| 47 | 0 | 42 | 3 | | | 44 | 0 | | |
| 50 | 0 | 43 | 1 | | | 48 | 0 | | |
| 52 | 0 | 53 | 0 | | | 51 | 0 | | |
| 57 | 0 | 55 | 0 | | | 54 | 0 | | |
| | | 58 | 1 | | | 56 | 0 | | |
| | 6 | | 18 | | 5 | | 4 | | 4 |
| ABC-J: 17 Days After the Start of Administration | | | | | | | | | |
| 2 | 0 | 3 | 0 | 6 | 1 | 1 | 1 | 9 | 0 |
| 4 | 0 | 5 | 1 | 11 | 0 | 7 | 0 | 22 | 1 |
| 8 | 0 | 12 | 0 | 17 | 0 | 13 | 0 | 33 | 0 |
| 10 | 0 | 16 | 1 | 27 | 0 | 15 | 1 | 46 | 1 |
| 14 | 0 | 20 | 0 | 35 | 0 | 18 | 0 | | |
| 19 | 0 | 23 | 0 | 45 | 1 | 21 | 0 | | |
| 25 | 0 | 26 | 1 | 49 | 0 | 24 | 0 | | |
| 29 | 0 | 30 | 0 | | | 28 | 0 | | |
| 34 | 0 | 32 | 0 | | | 31 | 0 | | |
| 36 | 0 | 37 | 0 | | | 38 | 0 | | |
| 41 | 0 | 40 | 0 | | | 39 | 0 | | |
| 47 | 0 | 42 | 2 | | | 44 | 0 | | |
| 50 | 0 | 43 | 0 | | | 48 | 0 | | |
| 52 | 0 | 53 | 0 | | | 51 | 0 | | |
| 57 | 0 | 55 | 0 | | | 54 | 0 | | |
| | | 58 | 0 | | | 56 | 0 | | |
| | 0 | | 5 | | 2 | | 2 | | 2 |

TABLE 4

| PARS-TR Item | | Before Administration | 17 Days After Administration |
|---|---|---|---|
| 25 | Persistently asking the same question | 1 | 0 |
| 26 | Showing confusion when regular daily routine of procedures suddnly change | 1 | 1 |
| 27 | Having negative lifestyle habits, and being incapable of living independently | 0 | 0 |
| 28 | Becoming mentally unstable when recalling bad events in the past | 2 | 1 |
| 29 | Showing extreme pickiness in food, with no extremely narrow range of food choice | 0 | 0 |
| 30 | Being disgusted with a particular sound | 2 | 1 |
| 31 | Being insensitive or sensitive to pain or heat | 0 | 0 |
| 32 | Being terrified of nothing | 0 | 0 |
| 33 | Suddenly crying or becoming upset | 1 | 0 |
| 34 | Showing self-harming behaviors, such as hitting the head on the wall or biting the hand | 0 | 0 |
| 35 | Having no friends of about the same age | 2 | 2 |
| 36 | Showing self-centered behaviors without regard for surrounding people | 1 | 0 |
| 37 | Showing interactive behaviors inappropriate for the context when approached by someone | 1 | 1 |
| 38 | Interacting with others only when having a request | 1 | 0 |
| 39 | Having difficulty understanding what is said from one situation to another | 0 | 0 |
| 40 | Using big words, but not fully understanding the meaning thereof | 0 | 0 |
| 41 | Difficulty understanding who is talking to who in a large group conversation | 0 | 0 |
| 42 | Being incapable of explaining how and why | 0 | 0 |

TABLE 4-continued

| PARS-TR Item | | Before Administration | 17 Days After Administration |
|---|---|---|---|
| 43 | Speaking in a unnatural and monotonous tone | 1 | 1 |
| 44 | Having difficulty understanding another person's feeling or point of view | 1 | 0 |
| 45 | Having difficulty understanding jokes and irony, and interpreting them literally | 1 | 1 |
| 46 | Being keen on acquiring knowledge in a particular field, such as the names of places or train stations | 2 | 1 |
| 47 | Enacting a familiar scene from a TV show alone | 0 | 0 |
| 48 | Persistently and repeatedly harassing someone on purpose | 0 | 0 |
| 49 | Always wanting to be the best | 0 | 0 |
| 50 | Showing tic symptoms (e.g., blinking, head movements, abuseful language) | 0 | 0 |
| 51 | Being restless in a manner inappropriate for the context | 0 | 0 |
| 52 | Being very careless, unable to behave appropriately for the context | 1 | 0 |
| 53 | Showing behavioral arrest, and becoming incapable of moving to the next act fo frozen | 0 | 0 |
| 54 | Appearing unashamed | 1 | 1 |
| 55 | Being easily deceived | 1 | 1 |
| 56 | Being likely to feel victimized, suspicious, or aggressive | 1 | 0 |
| 57 | Being emotionally unstable, and showing frequent emotional ups and downs | 1 | 0 |
| | Total Score of Items 25 to 57 | 22 | 11 |

As shown in Table 3 and FIG. 6, the diagnosis by ABC-J indicates that the administration of the test drug significantly improved symptoms across all of the 5 subscales I to V (Irritability, Lethargy, Stereotypical Behavior, Hyperactivity, and Inappropriate Speech). In particular, improvement was observed in symptoms under subscale III (Stereotypical Behavior) (in particular, symptoms stated in items 6, 35, and 45), symptoms under subscale V (Inappropriate Speech) (in particular, symptoms stated in items 22 and 46), and symptoms under subscale II (Lethargy) (in particular, symptoms stated in items 5, 16, 20, 30, 37, 40, 42, 43, and 58), which are closely related to diagnostic criteria of DSM-5 (mainly A and B) and are characteristic symptoms in ASD. In subscale I (Irritability) as well, symptoms stated in items 4, 10, 14, and 25 improved to the point of "0=no problem" by the intake of the test drug for 17 days.

From the assessment results based on PARS-TR items shown in Table 4, the administration of the test drug was confirmed to have improved ASD, showing a significant decrease in the sum of the scores of items 25 to 57 to 11 from 22 (see Table 2).

Example 3: Administration of Pyridoxamine Compound to ASD Patient (Case 3)

A pyridoxamine compound was administered to an ASD patient with severe intellectual disabilities and hyperacusis, who was not the subject in Example 1 or 2, and the effect in improving symptoms of ASD brought about by the administration was examined in an exploratory manner.

1. Method

An ASD patient (female, 13 years old, body weight: 45 kg) orally took the test drug detailed below every day for 8 weeks, and her symptoms of ASD were assessed by the diagnostic method described below before (before the start of administration) and 8 weeks after the intake of the drug (8 weeks after the start of administration).

Test Drug

Pyridoxamine Dihydrochloride: twice a day after breakfast and dinner, every day, 400 mg/dose (800 mg/day)

Vitamin $B_1$ (Fursultiamine): one time a day after breakfast every day when taking the pyridoxamine, 25 mg/dose (25 mg/day)

Diagnostic Method

The symptoms of ASD of the ASD patient were assessed based on the scores of ABC-J, PARS-TR, and RSB-R (Japanese version) by a medical doctor who is a researcher of ASD.

2. Results

FIGS. 7A and 7B show a comparison in the total score of all ABC-J items and the total score of each subscale (Irritability, Lethargy, Stereotypical Behavior, Hyperactivity, and Inappropriate Speech) between before and 8 weeks after the intake of the drug by the test subject. As shown in the figures, the administration of the test drug decreased both the total score of all ABC-J items and the total score of each of the 5 subscales compared with the scores before the administration, indicating that all of the ASD symptoms significantly improved.

As with ABC-J, RBS-R also exhibited a significant decrease in both the total score and the total score for each subscale (Stereotypical Behavior, Self-Harming Behavior, Obsessive-Compulsive Behavior, Ritualized Behavior, Insistence on Sameness, and Circumscribed Interests) 8 weeks after the intake, compared with the scores before the intake (FIGS. 8A and 8B), indicating that the administration of the drug significantly improved all of the ASD symptoms.

In diagnosis by PARS-TR, the score in early childhood peak was 32, and the current score in early adolescence or adulthood before the intake of the drug was 21, both exceeding the cutoff scores shown in Table 2. However, 18 weeks after the intake, the current score in early adolescence or adulthood decreased to 14, which is significantly lower than the cutoff score (20).

Although the subject of case 3 had severe intellectual disabilities and hypersensibility, the intake of the test drug lowered the severity of hypersensitivity and decreased the sense of difficulty in everyday life. Specifically, before the intake of the drug, the test subject exhibited hyperacusis: after being surprised by someone's sudden fit of coughing in school or at home, the subject approached the person coughing, and hit him or her (item 30 (rating 2)). However, 8 weeks after the intake of the test drug, the subject remained calm both in school and at home when someone suddenly started to cough, which previously surprised her and drove her to hit the person (item 30 (rating 1)). She also had to continuously cover her ears when traveling along an expressway in a family car because of the noise (item 30 (rating 2)). However, 8 weeks after the intake of the test drug, she became tolerant of traveling on an expressway by car without covering her ears (item 30 (rating 1)). Before the intake of the test drug, she also hated the movement of windshield wipers, or was too frightened by a ceiling fan to approach the underside of the fan (item 32 (rating 1)). However, 8 weeks after the intake of the test drug, she was still somewhat worried about the fan, but was no longer frightened (item 32 (rating 0)). Because of the decreased severity of hypersensibility including auditory sensitivity, she became able to spend every day in a state of ease. In addition, the subject of case 3 was insensitive to pain before the intake of the drug (item 31 (rating 1)), the degree of insensitivity was relieved 8 weeks after the intake of the test drug internal (item 31 (rating 1)). This sort of "hyper- or hyporeactivity to sensory input or unusual interests in sensory aspects of the environment" are characteristic symptoms of ASD stated in diagnostic criteria B(4) of DSM-5. The results of this Example reveal that the composition of the present invention can significantly improve the characteristic symptoms of ASD.

Example 4: Administration of Pyridoxamine Compound to ASD Patient (Case 4)

With an ASD patient showing no speech with severe intellectual disability, who is not the subject of Examples 1 to 3, the effect of the administration of a pyridoxamine compound in improving symptoms of ASD was examined in an exploratory manner.
1. Method
An ASD patient (male, 16 years old, body weight: 48 kg) took the following test drug orally for 8 weeks daily. The symptoms of ASD were assessed before the intake (before the start of administration) and 8 weeks after the intake (8 weeks after the start of administration) in accordance with the following diagnostic method.
Test Drug
Pyridoxamine Dihydrochloride: taken twice daily, after breakfast and after dinner, 400 mg/dose (800 mg/day)
Vitamin $B_1$ (Fursultiamine): taken once daily after breakfast when pyridoxamine was taken, 25 mg/dose (25 mg/day)
Diagnostic Method
The ASD symptoms of the ASD patient were assessed based on the scores in ABC-J and RSB-R (Japanese version) by a medical doctor who is a researcher of ASD.
2. Results
FIGS. 9A and 9B show the results of a comparison of the total score of all items of ABC-J and a comparison of the subtotal score of subscale items (Irritability, Lethargy, Stereotypical Behavior, Hyperactivity, Inappropriate Speech) observed in this test subject between before the intake and 8 weeks after the intake. As shown in the figures, the total score of all items and every subtotal score of the four subscales decreased compared with the scores before the administration, and the administration of the test drugs was confirmed to have significantly improved all of the assessed symptoms of ASD. In this case, the score of the item "Inappropriate Speech" was zero, because the subject showed no speech.

As with ABC-J, the total score of all items in RBS-R and the total score of subscale items (Stereotypical. Behavior, Self-Harming Behavior, Obsessive-Compulsive Behavior, Insistence on Sameness) 8 weeks after the intake significantly decreased, compared with the scores before the intake (FIGS. 10A and 10B), and the administration of the test drugs was confirmed to have significantly improve the symptoms of ASD.

Although the subject of this case was an ASD patient with severe intellectual disability, showing no speech, the intake of the test drugs alleviated the severity of irritability and self-harming behavior, and improved the sense of everyday difficulty. In particular, the intake of the test drug was confirmed to have significantly improved the stereotypical behaviors, which are characteristic symptoms of ASD stated in diagnostic criteria B(l) of DSM-5.

Experimental Example 1: Experiment on Capture of Serotonin or Dopamine by Glyoxal To examine whether a test compound (pyridoxamine or pyridoxal) inhibits capture of brain amines (serotonin or dopamine) by a carbonyl compound (glyoxal), the following experiment was performed.
1. Method
Reaction solutions were prepared by mixing components as shown in Table 5 such that 10 mol of glyoxal (GO: 40% glyoxal solution, Wako Pure Chemical Industries, Ltd.) and/or 10 mol of a test compound (pyridoxal (PL) or pyridoxamine (PM)) are present per mol of serotonin (5-HT: serotonin hydrochloride, Sigma-Aldrich Japan) or dopamine (DP: dopamine hydrochloride, Wako Pure Chemical Industries, Ltd.). The reaction solutions are incubated at room temperature, and the amount of free serotonin or dopamine, which were not captured by glyoxal, in the reaction solutions was measured by HPLC.

The negative control contained only 5-HT or DP with a buffer (GO and the test compounds were not added) (test samples 1 and 5), and the positive control contained 5-HT or DP and only GO (none of the test compounds was added) (test samples 2 and 6). The incubation time period for the test samples 1 to 4, to which 5-HT was added, was 2 hours, and the incubation time period for the test samples 5 to 8, to which DP was added, was 30 minutes. After incubation, the reaction solutions were diluted 10-fold (pH 7.4) with a 0.25 M phosphate buffer, and analyzed by HPLC. The HPLC analysis was performed with instruments produced by Shimadzu Corporation (system controller: SCL-10A vp, auto injector: SIL-10A, degasser: DGU-12A, liquid chromatograph: LC-10AD vp, UV-Vis detector: SPD-10A vp, and column oven: CTO-10AC vp) under the conditions shown in Table 6. The data analysis was performed with Chromatopac C-R7A Plus.

TABLE 5

| Formulation of Reation Solutions: Final Concentration | | | | | | | | |
|---|---|---|---|---|---|---|---|---|
| | Test Sample | | | | | | | |
| | 1 | 2 | 3 | 4 | 5 | 6 | 7 | 8 |
| Serotonin (5-HT) | 2.5 mM | 2.5 mM | 2.5 mM | 2.5 mM | — | — | — | — |
| Dopamine (DP) | — | — | — | — | 2.5 mM | 2.5 mM | 2.5 mM | 2.5 mM |
| Glyoxal (GO) | — | 25 mM | 25 mM | 25 mM | — | 25 mM | 25 mM | 25 mM |

TABLE 5-continued

Formulation of Reation Solutions: Final Concentration

| | Test Sample | | | | | | | |
|---|---|---|---|---|---|---|---|---|
| | 1 | 2 | 3 | 4 | 5 | 6 | 7 | 8 |
| Pyridoxal (PL) | — | — | 25 mM | — | — | — | 25 mM | — |
| Pyridoxamine (PM) | — | — | — | 25 mM | — | — | — | 25 mM |
| 0.25M Phosphate Buffer (pH 7.4) | 33 v/v % | 33 v/v % | 33 v/v % | 33 v/v % | 33 v/v % | 33 v/v % | 33 v/v % | 33 v/v % |

TABLE 6

HPLC Conditions

| | |
|---|---|
| Column | Puresil 5µ C18 120Å 4.6 × 150 mm (Waters) |
| Solvent A | 0.1% Trifluoroacetic Acid (TFA) Aqueous Solution |
| Solvent B | 0.08% TFA added 80% Acetonitrile Aqueous Solution |
| Flow Rate | 0.800 ml/min |
| Column Temperature | 30° C. |
| Detection | UV 254 nm |
| Gradient of Solvent | Solvent A: Solvent B = 100:0 to 30:70/20 min |

2. Results

Figure 11:
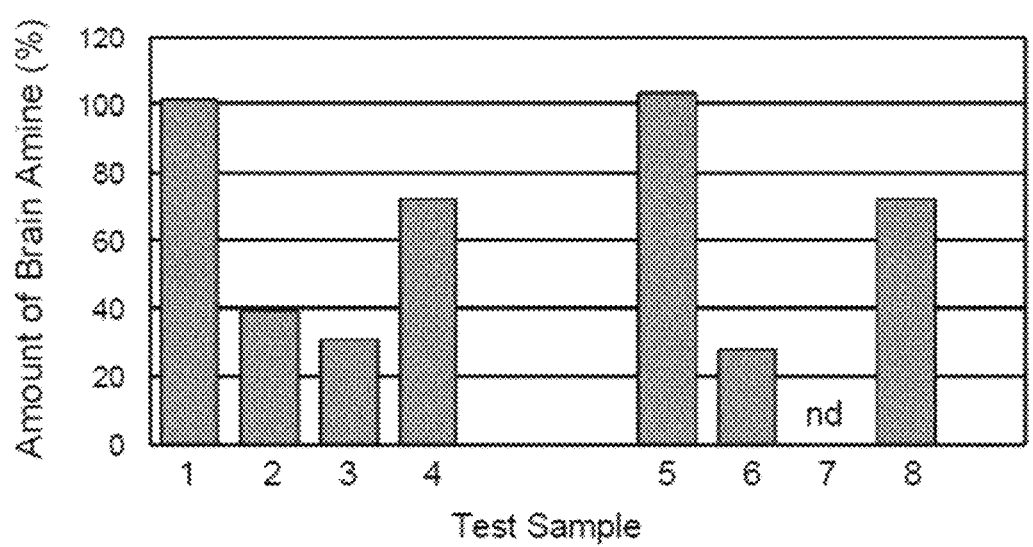
FIG. 11 illustrates results that confirm whether pyridoxal and pyridoxamine can inhibit glyoxal (a carbonyl compound) from capturing the amine (serotonin and dopamine) in the brain (Experimental Example 1). The vertical axis indicates the amount of amine in the brain relative to the results of a negative control (the amine amount in the brain; test sample 1 or 5) taken as 100%. In the figure, "nd" indicates no detection.

FIG. 11 shows the experimental results. The amount of the brain amine (serotonin or dopamine) is indicated by a value relative to the negative control (test samples 1 and 5) taken as 100%. In the positive control prepared by adding glyoxal to serotonin or dopamine (test samples 2 and 6), detected free serotonin was only about 40% that of the negative control (test sample 2), and detected free dopamine was only about 30% that of the negative control (test sample 6). This indicates that the brain amines were captured by a carbonyl compound. In the presence of pyridoxamine, despite the presence of glyoxal, the amount of free serotonin or the amount of free dopamine was recovered to about 70% that of the negative control (test samples 4 and 8). This reveals that pyridoxamine significantly inhibits the capture of brain amines by a carbonyl compound. However, when pyridoxal was added, the amount of free serotonin or free dopamine was rather decreased (test samples 3 and 7); and because of the presence of pyridoxal, no free dopamine became detectable in test sample 7, to which dopamine was added.

The results confirm that pyridoxal facilitates the decrease of brain amines, such as serotonin and dopamine, leading to the depletion of the amines. The probable reason, while not wishing to be limited or bound by theory, but simply as conjecture, is that the carbonyl groups of pyridoxal react with the amino groups of serotonin or dopamine to form Schiff bases. If that is the case, pyridoxal would react not only with brain amines but also with biologically critical compounds, such as thiamine, to deplete these compounds, possibly leading to a neurological disorder.

Figure 12:
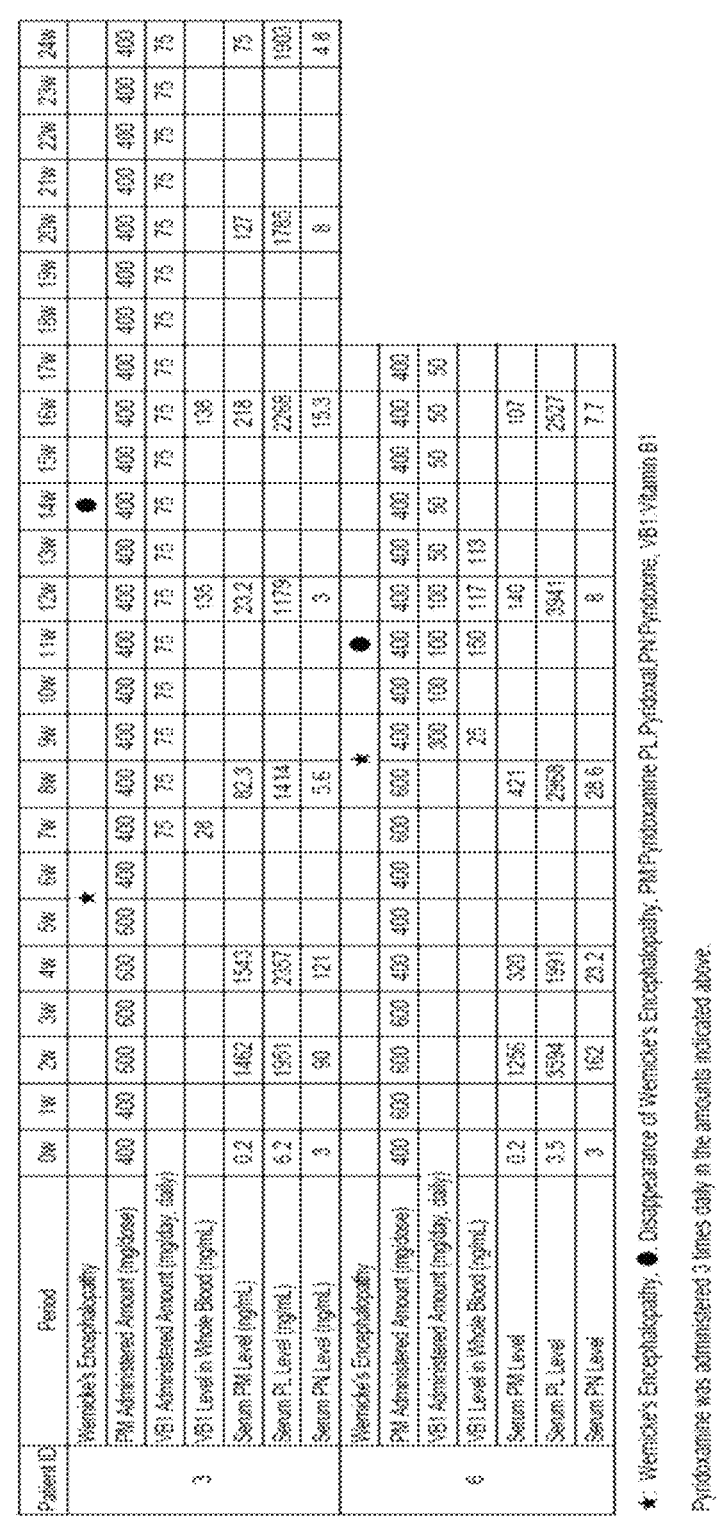

Reference Experimental Example 1: Treatment of Vitamin $B_1$ Deficiency that Occurs on Pyridoxamine Compound Medication FIG. 12 shows changes in the vitamin $B_1$ (VB1) level in whole blood, serum pyridoxamine (PM) level, serum pyridoxal (PL) level, and serum pyridoxine (PN) level of two test subjects (patient ID: No. 3, 61 years old, body weight 43 kg; and patient ID: No. 6, 62 years old, body weight 44 kg; both subjects have schizophrenia), who developed vitamin $B_1$ deficiency (Wernicke's encephalopathy) during the dosing period of a pyridoxamine compound (pyridoxamine dihydrochloride) (hereinafter, simply "medication") (0 to 24 weeks), in accordance with a medication protocol.

The measurement of the vitamin $B_1$ level in whole blood (blood collection with heparin), serum pyridoxamine level, serum pyridoxal level, and serum pyridoxine level was outsourced (SRL, Inc., LSI Medience Corporation), and performed by LC/MS/MS.

In accordance with the protocol shown in FIG. 12 (shown in the "PM Administered Amount (mg/dose)" row of FIG. 12), the test subjects took pyridoxamine dihydrochloride (a pyridoxamine compound) orally in an amount of 400 mg or 600 mg at a dose three times daily (morning, afternoon, and before bedtime) every day (the dosage of pyridoxamine per day: about 830 mg or 1250 mg).

The test subject with ID No. 3 developed an epilepsy-like symptom 6 weeks after the start of administration, and was examined with a brain MRI. The results showed a sign suggestive of Wernicke's encephalopathy. The vitamin $B_1$ level in whole blood of the test subject at this time was 28 ng/mL, which is near the lower limit of the baseline (24-66 ng/mL). This suggested that the subject developed vitamin $B_1$ deficiency during medication. The serum pyridoxamine level of the test subject 4 weeks after the start of administration was 1543 ng/mL, which was about 7700 times higher than the level at the start of administration. The serum pyridoxal level was 2357 ng/mL, which was about 380 times higher than the level at the start of administration. After the finding suggestive of Wernicke's encephalopathy, oral administration of a thiamine compound (Fursultiamine, Takeda Pharmaceutical Company, Ltd.) was immediately started at a dose of 75 mg/day (administration once daily), and continued every day. As a result, the vitamin $B_1$ level in whole blood increased to 135 ng/mL 12 weeks after the start of administration (6 weeks after the start of administration of the thiamine compound). Additionally, despite the continuous daily administration of a pyridoxamine compound, the serum pyridoxamine level at this time was 23.2 ng/mL, and the serum pyridoxal level was 1179 ng/mL, both of which were lower than those 4 weeks after the start of administration. 14 weeks after the start of administration (8 weeks after the start of administration of the thiamine compound), the symptom of Wernicke's encephalopathy disappeared.

The test subject with ID No. 6 was examined with a brain MRI 9 weeks after the start of administration, and showed signs suggestive of Wernicke's encephalopathy. The vitamin $B_1$ level in whole blood of the test subject at this time was 25 ng/mL. The serum pyridoxamine level of the test subject 8 weeks after the start of administration was 421 ng/mL, which was about 2100 times higher than the level at the start of administration. The serum pyridoxal level was 2968 ng/mL, which was about 850 times higher than the level at the start of administration. After the finding suggestive of Wernicke's encephalopathy, intravenous administration of a thiamine compound (Fursultiamine, Takeda Pharmaceutical Company, Ltd., 300 mg/day) was immediately started, and thereafter (10 weeks after the start of administration), oral administration of a thiamine compound at a dose of 100 to 50 mg/day continued. As a result, the vitamin $B_1$ level in whole blood was increased to 150 ng/mL 11 weeks after the start of administration (3 weeks after the administration of the thiamine compound), and the symptoms of Wernicke's encephalopathy disappeared. At this time, the serum pyridoxamine level was 140 ng/mL, and the serum pyridoxal level was 3941 ng/mL.

These cases suggest that high-dose administration of a pyridoxamine compound may evoke vitamin $B_1$ deficiency. However, the administration of a thiamine compound in parallel with the administration of a pyridoxamine compound leads to the disappearance of Wernicke's encephalopathy symptoms, preventing the development of the disease, regardless of a high dose of the at least one pyridoxamine compound.

Reference Experimental Example 2: Kinetics of Pyridoxamine Compound in Blood

As shown in Reference Experimental Example 1, the administration of a pyridoxamine compound increases not only the pyridoxamine level in blood, but also the pyridoxal level in blood. Rather, in blood, the pyridoxal level was higher than the pyridoxamine level. Thus, the following describes the observation results regarding changes in the plasma level of pyridoxamine (an unchanged substance) and its metabolites (pyridoxal (PL), pyridoxine (PN), and 4-pyridoxic acid (4-PA)) after the administration of a pyridoxamine compound. The observation results were obtained in a clinical trial performed by collaborators of the applicant of this application, and are shown here simply for reference.

Specifically, 18 test subjects (healthy male adults) were divided into the following 3 groups according to the dose of pyridoxamine (300 mg/dose, 600 mg/dose, 900 mg/dose), and these subjects were orally administered pyridoxamine dihydrochloride (administered three times daily: at 0 hours, at 6 hours, and at 12 hours).
Group 1: administered pyridoxamine at a dose of 300 mg (average age: 25.0 years old, average height: 172.55 cm, average body weight: 59.92 kg, average BMI: 20.12)
Group 2: administered pyridoxamine at a dose of 600 mg (average age: 25.5 years old, average height: 172.30 cm, average body weight: 61.97 kg, average BMI: 20.80)
Group 3: administered pyridoxamine at a dose of 900 mg (average age: 23.8 years old, average height: 171.55 cm, average body weight: 59.65 kg, average BMI: 20.23).

The blood of the subjects of each group was collected at predetermined time points after the start of oral administration to collect plasma, and the plasma levels of pyridoxamine, pyridoxal (PL), pyridoxine (PN), and 4-pyridoxic acid (4-PA) were measured by LC-MS-MS.

FIG. 13A (pyridoxamine) and FIG. 13B (pyridoxal), and FIG. 14A (4-pyridoxic acid) and FIG. 14B (pyridoxine) show the results. As shown in FIG. 13A, the plasma level of pyridoxamine (unchanged substance) reached a peak 3 hours after the administration of pyridoxamine dihydrochloride, and then decreased. As shown in FIGS. 13B and 14A, 4 to 6 hours after the administration of pyridoxamine, as if replacing the peak of pyridoxamine, the pyridoxal (PL) and 4-pyridoxic acid (4-PA) levels reached a peak. The plasma levels of pyridoxamine, pyridoxal, and 4-pyridoxic acid increased along with the increase in dose of pyridoxamine dihydrochloride. However, pyridoxine (PN) did not show any substantial change (FIG. 14B). The results reveal that most of the pyridoxamine absorbed into the body transformed into pyridoxal or 4-pyridoxic acid.

Figure 15:
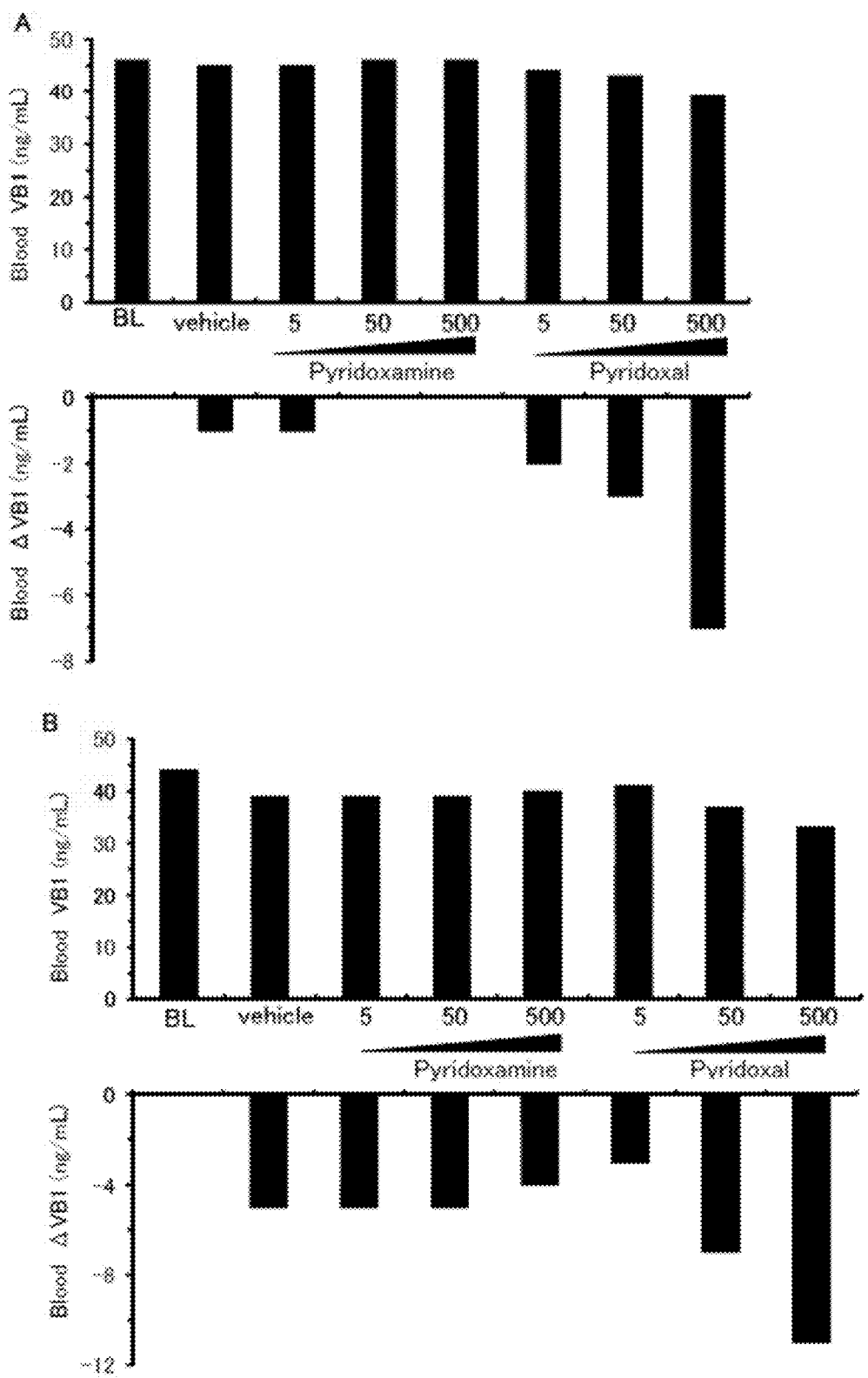
FIG. 15 illustrates changes in the vitamin $B_1$ level in human whole blood (sample) to which pyridoxamine dihydrochloride (final concentration: 5, 50, 500 μg/mL) or pyridoxal hydrochloride (final concentration: 5, 50, 500 μg/mL) was added.

Reference Experimental Example 3: Effect of Pyridoxamine and Pyridoxal on Vitamin $B_1$ Level in Whole Blood Since Reference Experimental Example 1 suggested that administration of a pyridoxamine compound potentially evokes vitamin $B_1$ deficiency, an in vitro test was performed to examine whether a pyridoxamine compound decreases the vitamin $B_1$ level in whole blood. Because the administration of a pyridoxamine compound increases not only the serum pyridoxamine level but also the serum pyridoxal level, as stated in Reference Experimental Examples 1 and 2, pyridoxamine and pyridoxal were both examined as a test substance.
1. Method Blood was collected from a human using EDTA-2K as an anticoagulant. Pyridoxamine dihydrochloride (Sigma-Aldrich Japan) as pyridoxamine and pyridoxal hydrochloride (Nacalai Tesque, Inc.) as pyridoxal were individually dissolved in physiological saline to give 0.5, 5, and 50 mg/mL, thereby preparing test solutions. 10 µL of each test solution was added to 1 mL of the collected whole blood (test samples). The final concentration of the test substance in each test sample was 5, 50, or 500 µg/mL. Additionally, 10 µl of physiological saline was added to 1 mL of whole blood to prepare a vehicle. The vehicle and test samples were incubated at 37° C. for 1 hour or 16 hours, and then immediately frozen. The vitamin $B_1$ levels in whole blood before incubation to which no physiological saline and test solution had been added (which may hereinafter be referred to as "baseline"; in FIG. 15, "BL"), the vehicle after incubation, and the test samples were measured by SRL, Inc. using LC/MS/MS.
2. Results FIG. 15 shows the measurement results. FIGS. 15A and 15B each show the results 1 hour after incubation and 16 hours after incubation. The upper charts of FIGS. 15A and 15B show the vitamin $B_3$ level in whole blood (ng/mL), and the bottom charts of FIGS. 15A and 15B show the difference of the vitamin $B_1$ level between the baseline and the samples after incubation ($\Delta$VB1) (ng/mL).

One hour after incubation, there was no change in the vitamin $B_1$ level in whole blood to which pyridoxamine dihydrochloride was added. However, there was a decrease in the vitamin $B_1$ level in whole blood to which pyridoxal hydrochloride was added, in a pyridoxal-hydrochloride-concentration-dependent manner (FIG. 15A).

Sixteen hours after incubation, there was a change in the vitamin $B_1$ level in whole blood to which pyridoxamine dihydrochloride was added, compared with the baseline. However, this decrease was substantially equivalent to the decrease observed in the vehicle, and did not appear to be dependent on the addition of pyridoxamine. There was a decrease in the vitamin $B_1$ level in whole blood to which pyridoxal hydrochloride was added in a pyridoxal hydrochloride-concentration-dependent manner (FIG. 15B).

The results reveal that pyridoxamine has no direct effect in decreasing the vitamin $B_1$ level in whole blood, but that pyridoxal has an effect in decreasing the vitamin $B_1$ level in whole blood.

As shown in Reference Experimental Examples 1 and 2, pyridoxamine is metabolized into pyridoxal when absorbed into the body. From this, it is speculated that the increase in the pyridoxal level in the body caused by the administration of a pyridoxamine compound decreases the vitamin $B_1$ level in the body leading to the development of symptoms of vitamin $B_1$ deficiency.

Reference Experimental Example 4: Prevention of Vitamin $B_1$ Deficiency by Administration of Pyridoxamine Compound in Combination with Thiamine Compound The results in Reference Experimental Example 3 highlighted the need for preventing vitamin $B_1$ deficiency when a pyridoxamine compound is administered.

To confirm the effect of the administration of a pyridoxamine compound in combination with a thiamine compound, 7 test subjects to which a pyridoxamine compound was administered (average age: 44.3 years old, average body weight: 55.4 kg) were also administered a thiamine compound in parallel. Specifically, the seven test subjects were orally administered 1200 to 1800 mg of pyridoxamine dihydrochloride per day as a pyridoxamine compound (administered at a dose of 400 to 600 mg three times per day) for 24 weeks, every day. The dose of 400 to 600 mg/day of pyridoxamine dihydrochloride is converted to 277 to 415 mg/day of pyridoxamine. Regarding the administration of a thiamine compound, the seven subjects were orally administered fursultiamine as a thiamine compound at a dose of 75 mg/day for 2 to 21 weeks after the start of administration of the pyridoxamine compound, and the administration continued every day until the end of the pyridoxamine compound administration.

As a result, all seven test subjects exhibited no sign suggestive of vitamin $B_1$ deficiency until the end of the administration of the pyridoxamine compound. This indicates that when administering a pyridoxamine compound, in particular a high dose of a pyridoxamine compound, it is preferable to administer a thiamine compound in combination.

The invention claimed is:

1. A method for inhibiting or improving symptoms in a subject with autism spectrum disorder,
the method comprising the step of administering at least one pyridoxamine compound selected from the group consisting of pyridoxamine and pharmaceutically acceptable salts thereof, or a preparation containing the at least one pyridoxamine compound to the subject, wherein the symptoms is at least one selected from behavioral disorders included in subscale I of ABC-J, and symptoms included in item (4) under diagnostic criteria B of DSM-5.

2. The method according to claim 1, wherein the daily dose (or intake) of the at least one pyridoxamine compound is, on a pyridoxamine amount basis, 10 mg or more in the case of a food or drink, and 300 mg or more in the case of an orally administered drug.

3. The method according to claim 1, further comprising the step of administering at least one thiamine compound selected from the group consisting of thiamine, derivatives thereof, and pharmaceutically acceptable salts thereof to the subject with autism spectrum disorder.

4. The method according to claim 3, wherein the daily dose (or intake) of the at least one thiamine compound is 1 to 500 mg on a thiamine amount basis.

5. The method according to claim 3, wherein the daily dose of the at least one thiamine compound is 1 to 20 parts by weight, per 100 parts by weight of the daily dose of the at least one pyridoxamine compound.

6. The method according to claim 3, wherein the at least one pyridoxamine compound and the at least one thiamine compound are each packaged alone, or with a pharmaceutically acceptable carrier or additive in separate preparations; and the at least one pyridoxamine compound or the preparation containing the at least one pyridoxamine compound and the at least one thiamine compound or the preparation containing the at least one thiamine compound are administered to the subject at different times, simultaneously, or in parallel.

7. The method according to claim 3, wherein the at least one pyridoxamine compound or the preparation containing the at least one pyridoxamine compound is administered to the subject before administration of the at least one thiamine compound or the preparation containing the at least one thiamine compound, or the at least one pyridoxamine compound or the preparation containing the at least one pyridoxamine compound is administered to the subject after administration of the at least one thiamine compound or the preparation containing the at least one thiamine compound.

8. The method according to claim 3, wherein the at least one pyridoxamine compound and the at least one thiamine compound are each packaged together with a pharmaceutically acceptable carrier or additive in the form of a combination drug prepared as a single preparation; and the at least one pyridoxamine compound or the preparation containing the at least one pyridoxamine compound and the at least one thiamine compound or the preparation containing the at least one thiamine compound are simultaneously administered to the subject with autism spectrum disorder.

9. The method according to claim 1, wherein the subject is one in childhood, early adolescence, or adulthood.

10. The method according to claim 3, wherein the subject is one in childhood, early adolescence, or adulthood.

11. The method according to claim 1, wherein the symptoms comprises at least one selected from behavioral disorders included in subscales II to V of ABC-J, in addition to at least one selected from behavioral disorders included in subscale I of ABC-J and symptoms included in item (4) under diagnostic criteria B of DSM-5.

12. The method according to claim 3, wherein the symptoms comprises at least one selected from behavioral disorders included in subscales II to V of ABC-J, in addition to at least one selected from behavioral disorders included in subscale I of ABC-J and symptoms included in item (4) under diagnostic criteria B of DSM-5.

* * * * *